US006372499B1

(12) United States Patent
Midoux et al.

(10) Patent No.: US 6,372,499 B1
(45) Date of Patent: Apr. 16, 2002

(54) POLYMERIC COMPLEXES FOR THE TRANSFECTION OF NUCLEIC ACIDS, WITH RESIDUES CAUSING THE DESTABILISATION OF CELL MEMBRANES

(75) Inventors: Patrick Midoux, Orleans; Michel Monsigny, Saint-Cyr-en Val, both of (FR)

(73) Assignee: I.D.M. Immuno-Designed Molecules (FR)

( * ) Notice: Subject to any disclaimer, the term of this patent is extended or adjusted under 35 U.S.C. 154(b) by 0 days.

(21) Appl. No.: 09/297,519

(22) PCT Filed: Nov. 10, 1997

(86) PCT No.: PCT/FR97/02022

§ 371 Date: May 3, 1999

§ 102(e) Date: May 3, 1999

(87) PCT Pub. No.: WO98/22610

PCT Pub. Date: May 28, 1998

(30) Foreign Application Priority Data

Nov. 15, 1996 (FR) .............................................. 96 13990

(51) Int. Cl.[7] .............................................. C12N 15/88
(52) U.S. Cl. .................. 435/455; 435/69.1; 435/320.1; 435/325; 424/486
(58) Field of Search ..................... 424/486; 435/320.1, 435/455, 325, 69.1; 514/44

(56) References Cited

U.S. PATENT DOCUMENTS

| 5,166,320 A | | 11/1992 | Wu et al. ..................... 530/395 |
| 5,733,762 A | * | 3/1998 | Midoux et al. .......... 435/172.3 |
| 5,846,530 A | * | 12/1998 | Soon-Shiong et al. ..... 424/93.7 |
| 5,977,084 A | * | 11/1999 | Szoka, Jr. et al. ............ 514/44 |
| 6,030,941 A | * | 2/2000 | Summerton et al. ........... 514/2 |

FOREIGN PATENT DOCUMENTS

| EP | 0350246 | | 1/1990 |
| EP | 0387775 | | 9/1990 |
| EP | 0388758 | | 9/1990 |
| FR | 2107756 | | 5/1972 |
| FR | 2719316 | | 11/1995 |
| WO | 9211037 | | 7/1992 |
| WO | 9213570 | | 8/1992 |
| WO | 95/30020 | * | 11/1995 |

OTHER PUBLICATIONS

Anderson, Human gene therapy, Nature, vol. 392, pp. 25–30, 1998.*
Verma et al., Gene therapy–promises, problems and prospects, Nature, vol. 389, pp. 239–242, 1997.*
Branch, A good antisense molecule is hard to find, TIBS, Feb. 23, 1998, pp. 45–50.*

Erbacher et al., Glycosylated Polylysine/DNA Complexes: Gene Transfer Efficiency in Relation with the Size and the Sugar Substituation Level of Glycosylated Polylysines and with the Plasmisd Size, Bioconjugate Chem., 1995, vol. 6, pp. 401–410.*
Erbacher et al., Gene Transfer by DNA/Glycosylated Polylsine Complexes into Human Blood Macrophages, Human Gene Therapy, vol. 7, Apr. 10, 1996, pp. 721–729.*
Kollen et al., Gluconoylated and Glycosylated Polylysines As Vector for Gene Transfer on Cystic Fibrosis Airways Epithelial Cells, Human Gene Therapy, vol. 7, Aug. 20, 1996, pp. 1577–1586.*
Mezo et al, "Carrier . . . Poly (L–Lysine)", Biopolymers, vol. 33, No. 6, 1993, pp. 873–885, XP002034603.
Wang et al, "Polyhistidine . . . Liposomes", Biochemistry, vol. 23, No. 19, 1984, pp. 4409–4416, XP002016041.
Midoux et al, "Specific . . . Cells", Nucleic Acids Research, vol. 21, No. 4, Feb. 25, 1993, pp. 871–878, XP000371764.
Biochemistry, 1984, 23, 4409–4416, XP002016041, Wang et al.
Biopolymers, vol. 33, 873–885, MEZO et al, XP002034603, 1993.

* cited by examiner

Primary Examiner—Dave T. Nguyen
(74) Attorney, Agent, or Firm—Bierman, Muserlian and Lucas

(57) ABSTRACT

The complex has at least one negatively charged nucleic acid bonded to at least one positively charged polymeric conjugate The conjugate containing a polylysine formed from monomers having free $NH_3^+$ groups, and having at least 10% of the free $NH_3^+$ groups substituted by residues which can be protonated in a weakly acid medium causing destabilization of cell membranes.

Optionally, some of the free $NH_3^+$ groups can be substituted by a molecule with a recognition signal by a cell membrane receptor.

The free $NH_3^+$ groups of the said polylysine make up at least 30% of the monomers of the polymeric conjugate.

The residue that causes the destabilization of cell membrane in weak acid of quinolines of the formula:

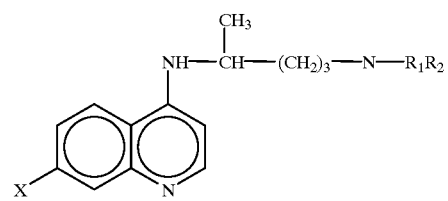

where $R_1$ is hydrogen, $R_2$ is $-(CH_2)_n 13\ CO_2-H$, X is hydrogen or chlorine and n is an integer from 1 to 10.

The signal is a simple oside or a disaccharide or peptide.

15 Claims, 9 Drawing Sheets

HispLK

I

II

POLYMERIC COMPLEXES FOR THE TRANSFECTION OF NUCLEIC ACIDS, WITH RESIDUES CAUSING THE DESTABILISATION OF CELL MEMBRANES

This application is a 371 of PCT/FR97/02022 filed Nov. 10, 1997.

The invention relates to new complexes of nucleic acids and polymer substituted by residues which cause destabilization of cell membranes.

The introduction of a foreign gene into a cell is the basis of genetic treatment. The transfer of genes can be achieved using either a modified viral material (vaccine virus, retrovirus, adenovirus or herpes virus) or using non-viral vectors (cationic lipids, liposomes). The former, although effective, have safety problems. As regards the latter, the effectiveness is greatly reduced in the presence of serum, and as a result their use is restricted to in vitro or ex vivo.

Polylysine, which can form stable electrostatic complexes with a plasmid DNA is the basis for development of non-viral vectors for transfer of genes in animal cells.

Complexes of DNA and unsubstituted polylysine generally are not effective for transfection of cells because of the very high stability of the complexes (and therefore weak dissociation and salting out of the DNA) under physiological conditions as a consequence of a very high co-operativity of polycation-polyanion interactions.

The transfection efficiency can be improved if the number of charges present on the polypeptide is decreased in order to reduce the interactive forces between the DNA and the polylysine. For example, if 40% of the $\epsilon$-$NH_3^+$ functions of the lysine residues of the polylysine are partly neutralized by polyhydroxyalkanoyl derivatives, such as $\delta$-gluconolactone, the DNA/partly gluconylated polylysine complexes are more effective than DNA/polylysine complexes in transfection of cells.

The polylysine can be substituted by specific receptor ligands which are present on the surface of cells and are capable of inducing specific endocytosis of complexes with a plasmid DNA by target cells.

Conjugates obtained by substituting polylysine by asialoorosomucoid, transferrin, insulin, immunoglobulin and growth factors have been proposed as plasmid guide vectors. However, these protein ligands render the complexes highly immunogenic.

The polylysine can be substituted by low molecular weight ligands which are less immunogenic than the osides and oligosides recognized by specific membrane receptors (membrane lectins) on the surface of target cells. Glycosylated polylysine has been proposed as non-viral vectors perfectly defined for transfer of genes.

Numerous animal cells have membrane lectins which recognize oligosides of various structures and which induce endocytosis of their ligands. For example, the membrane lectin of cells of the hepatic parenchyma recognize glucidic structures carrying a galactose residue in the terminal position, which is the case for the desialylated serum glycoproteins. The specificity of membrane lectins depends on the cell type and the state of differentiation of the cells.

The transfection efficiency of DNA/glycosylated polylysine complexes depends on the level of substitution of the polylysine by osides: The most effective transfections are obtained if 30 to 40% of the $\epsilon$-$NH_3^+$ functions of the lysine residues of the polylysine are substituted by mono- or disaccharides.

In French Patent no. 2,719,316, it has been shown that the use of partly gluconylated polylysine carrying an already reduced number of positive charges allows the number of osides required for bonding on the polymer to obtain a good transfection efficiency of DNA/glycosylated and gluconylated polylysine complexes to be decreased by a factor of 5 to 10. The use of partly gluconylated polylysine allows the solubility of complexes to be increased and their size to be reduced to about 50 nm.

The transportation of plasmids by non-viral vectors which can be recognized specifically by compounds of the plasma membrane of cells is dependent on a step which imitates the mechanism of entry of viral genetic material into a cell. In all the cases described, the DNA/polycationic polymer complexes are carried into endocytosis vesicles, into endosomes and probably into other deeper intracellular compartments removed from the plasma membrane.

The transmembrane passage of plasmid DNA is consequently a critical stage with respect to the release of the said DNA into the cytosol for its passage into the nucleus where the gene will be expressed.

In all the cases described, transmembrane passage auxiliaries are used to promote passage of the DNA into the cytosol. These are:

chloroquine defective adenoviruses permeabilizing and/or fusiogenic peptides a) Chloroquine is a weak base used in an amount of 50 $\mu$M or 100 $\mu$M in culture in vitro and for some cells these concentrations are toxic. Chloroquine, which permeates, crosses the membrane and accumulates in the acid compartments because it carries amines of low pK which capture protons; protonated chloroquine is cationic and less permeating. Acidification of endosomes and lysosomes is caused by a membrane enzyme which injects $H^+$ from cytosol into vesicles; to re-establish electroneutrality, this proton accumulation is accompanied by an entry of chloride ions $Cl^-$. To the extent that chloroquine accumulates, protons and chlorides also accumulate, which causes an increase in the intravesicular ionic force, which induces the arrival of water, resulting in swelling of the vesicles and their destabilization. The intracellular concentration of chloroquine can be more than 100 times higher than its concentration in the medium after a few hours. It can thus exceed 10 mM. This phenomenon is comparable to that which occurs in persons who use a daily dose of 300 mg chloroquine per day. After a few days, the plasma concentration is about 0.7 $\mu$M and the tissue concentration is 200 to 700 times higher, that is to say 140 to 500 $\mu$M. Inside the cells, the acid compartments can reach concentrations several tens of times higher. It is furthermore known that chloroquine concentrations of 10 mM (concentration obtained a few hours after having used an initial chloroquine concentration of 100 $\mu$M) promote dissociation of DNA/polylysine complexes.

Chloroquine in combination with DNA/polylysine complexes in gene transfer can be used only in applications in vitro or ex vivo, because of its toxicity and its rapid dilution after injection into the individual. In fact, in vivo, to achieve the high concentrations mentioned above, several days are necessary. It has thus been found in vitro that in cells pretreated with chloroquine, expression of the transferred genes was very low. In addition, if the chloroquine is added more than three hours after the incubation of the cells in the presence of the complexes, the transfection is very low. For these reasons chloroquine, which is a very good auxiliary in vitro, is not effective in vivo.

b) The fusiogenic properties of defective adenovirus particles in an acid medium are used to promote passage of DNA into the cytosol from endocytosis vesicles. Adenoviruses have fusion proteins which are active in a slightly acid medium. Defective adenoviruses can be used in the free form or bonded to DNA/polylysine complexes.

However, the use of even defective viral particles presents safety problems. Adenoviruses induce a very strong immune response after injection with the complexes.

c) Peptide which are permeabilizing and/or fusiogenic in a slightly acid medium are used as auxiliaries to promote passage of DNA into the cytosol. These are mainly peptides of 20 amino acids derived from virus fusion proteins, such as, for example, the N-terminal peptide of the sub-unit HA2 of the haemagglutinin of the influenza virus, or synthetic peptides, such as GALA (SEQ ID NO:1), an oligomer containing several recurring units of Glu-Ala-Leu-Ala (SEQ ID NO:1). These peptides are most often used in the free form (that is to say not covalently bonded) with the DNA/polylysine complexes. The efficiency of peptides is greatly reduced in the presence of serum in the cell culture medium, which restricts their use to experiments in vitro or to ex vivo. Some peptides covalently bonded to DNA/polylysine complexes are still effective in promoting transmembrane passage of DNA, while others lose their permeabilizing power after bonding.

It is furthermore known that there are other molecules which are capable of destabilizing membranes, and in particular molecules containing the imidazole nucleus of histidine (pK=6.04), which, by being protonated in a slightly acid medium, become cationic. Polyhistidine has fusiogenic and permeabilizing properties with respect to lipid bilayers. At pH<6, polyhistidine adopts an α-helical structure (Norland K. S. et al. (1963) Biopolymers 1:277–278; Beychok S. et al. (1965) J. Amer. Chem. Soc. 87:3990–3991). It has been shown that in a slightly acid medium polyhistidine is a polycation which aggregates negatively charged liposomes and induces their fusion (Wang C.-Y. and Huang L. (1984) Polyhistidine mediates an acid-dependent fusion of negatively charged liposomes. Biochemistry 23:4409–4416; Uster P. S. and Deamer D. W. (1985) pH-dependent fusion of liposomes using titrable polycations. Biochemistry 24:8–14).

It is known that a synthetic polymer (cetylacetyl (imidazol-4-ylmethyl)polyethyleneimine) induces the fusion of liposomes at a slightly acid pH (Oku N. et al. (1987) Low pH induced membrane fusion of lipid vesicles containing proton-sensitive polymer. Biochemistry 26:8145–8150).

It is also known that a neutral water-soluble polymer substituted by histidyl residues (used instead of polyhistidine, which is very poorly soluble in an aqueous medium) interacts with a polyanion, such as polyaspartic acid, only in a slightly acid medium and is capable of permeabilizing the plasma membrane of cells in a flow cytometry test using ethidium bromide as a marker (Midoux et al., 1995).

Preliminary results have shown that polyhistidine (very poorly soluble in an aqueous medium at neutral pH) cannot be used to transfect cells because, since it is not a polycation at neutral pH, it is not capable of forming with DNA stable complexes of sufficient solubility to be used at neutral pH, in particular at pH 7.4, the pH of plasma.

The invention relates to new complexes of nucleic acid and substituted polymer which are capable of transfecting several types of cells.

The invention relates to a new type of cationic polymer comprising, in addition to positive charges of the polymer, substituents which promote transmembrane passage of the nucleic acid transported and, where appropriate, substituents which act as recognition signals. The substituents which promote transmembrane passage are bonded to the polymer and are derivatives which are not cationic in a slightly alkaline medium but become so in a neutral medium and in an acid medium.

The invention relates to new complexes of nucleic acid and substituted polymer which are capable of promoting transmembrane passage of DNA after endocytosis of the complexes.

The invention relates to new complexes of nucleic acid and substituted polymer having no recognition signals recognized by membrane receptors on the surface of cells.

The invention relates to new complexes of nucleic acid and substituted polymer also having recognition signals recognized by membrane receptors on the surface of cells, conferring a selective transfection character with respect to various cell types.

The invention relates to a process for specific transfection in vitro and in vivo.

The invention relates to new conjugates of substituted polylysine having no recognition signals recognized by membrane receptors on the surface of cells, which are capable of being complexed with a nucleic acid for the purpose of transfection of a cell.

The invention also relates to new conjugates of polylysine also having recognition signals recognized by membrane receptors on the surface of cells, which are capable of being complexed with a nucleic acid for the purpose of selective transfection of a cell.

The advantage of the invention is that these new complexes of nucleic acid and polymer are capable of transfecting cells in the absence of transmembrane passage auxiliaries (chloroquine or permeabilizing and/or fusiogenic peptides). These are weakly basic groupings which can be protonated (cation) in a slightly acid medium and are bonded to the polymer and play the role of transmembrane passage auxiliaries.

The advantage of the invention is that these new complexes of nucleic acid and substituted polymer are as effective as or, without transmembrane passage auxiliaries, more effective than the complexes of nucleic acid and polymer which is unsubstituted or substituted by agents which reduce the number of charges on the polymer (and therefore its interaction with the nucleic acid) in the presence of transmembrane passage auxiliaries.

In the case of chloroquine and permeabilizing and/or fusiogenic peptides, the latter are small molecules which diffuse rapidly if they are not covalently bonded to complexes of nucleic acid and substituted polymer.

The advantage of the invention is that these new complexes of nucleic acid and substituted polymer are, in the presence of serum, just as effective as (or even more effective than) in the absence of serum for transfection of cells.

In one of its most general definitions, the invention relates to a complex between at least one (negatively charged) nucleic acid and at least one positively charged polymeric conjugate, the bond between the nucleic acid and the polymeric conjugate being electrostatic in nature and the polymeric conjugate containing a polymer formed from monomer units carrying free $NH_3^+$ functions, and being such that:

the free $NH_3^+$ functions of the abovementioned monomer units are substituted in a ratio of at least 10%, advantageously about 15% to about 45%, in particular 35%, this ratio being determined, for example, by nuclear magnetic resonance, by residues which can be protonated in a weakly acid medium causing destabilization of cell membranes, in particular the membrane of endocytosis vesicles, and/or of endosomes in a weakly acid medium, the abovementioned residues also having the following properties:

they carry a functional group which enables them to be bonded to the abovementioned polymer, they are not active with respect to the recognition signal recognized by a cell membrane receptor, they can carry at least one free $NH_3^+$ function, it being possible for the free $NH_3^+$ functions of the abovementioned monomer units also to be substituted by non-charged residues causing a reduction in the positive charges with respect to the same unsubstituted polymeric conjugate, facilitating salting out of the nucleic acid in the course of dissociation of the complex, the abovementioned non-charged residues also having the following properties:

they carry at least one hydroxyl group, they are not active with respect to the recognition signal recognized by a cell membrane receptor, molecules constituting a recognition signal recognized by a cell membrane receptor optionally being present:

by substitution of some of the free $NH_3^+$ functions of the abovementioned monomer units (for example $\epsilon$-$NH_3^+$ of lysine), or on some of the abovementioned non-charged residues causing a reduction in the charge (for example gluconyl), in particular on the hydroxyl groups of the abovementioned residues, or on some of the abovementioned residues causing a destabilization of cell membranes (for example acetylimidazole), or by substitution of the optional free $NH_3^+$ function of the abovementioned residues causing a destabilization of cell membranes (for example histidine), with the proviso that all the free $NH_3^+$ functions make up at least 30% of the number of monomer units of the polymeric skeleton of the abovementioned polymeric conjugate.

Destabilization of membranes is understood as meaning a modification of the membrane which leads either to an increase in its permeability with respect to low molecular weight and possibly high molecular weight molecules of the solution (including nucleic acids, plasmids or complexes), or fusion with another membrane.

The membrane permeability can be measured by fluorescence microscopy in the following manner:

Adhesive cells are incubated at 37° C. for 15 to 30 minutes with 0.5 ml DMEM culture medium with serum containing 5 mg/ml dextran (Mw 4,000) labelled with fluorescein isothiocyanate (FTC-dextran) and a DNA/histidylated polylysine complex. The cells are then washed and incubated at 37° C. for 15 to 30 minutes with culture medium comprising 10% foetal bovine serum. The cells are then fixed for 5 minutes in a saline phosphate buffer solution comprising 4% p-formaldehyde and the fluorescence is analysed with a confocal fluorescence microscope (MRC600 BioRad). In the absence of membrane permeabilization, the fluorescence originating from FTC-dextran is located exclusively in the vesicles. In the presence of a membrane permeabilization agent, the fluorescence originating from the FTC-dextran is also observed in a diffuse manner in the cytosol and the nucleus of the cells.

The fusion of membranes in the presence of DNA/histidylated polylysine complexes is measured easily in model systems, such as liposomes, using a lipid mixture method such as that described in Struck D. K. et al (Use of resonance energy transfer to monitor membrane fusion. (1981) Biochemistry 20:4093–4099). Briefly, liposomes made up of dioleoyl-phosphatidylcholine (DPOC), into the membrane of which are inserted N-(7-nitrobenz-2-oxa-1,3-diazol-4-yl)phosphatidylethanolamine (NBD-PE) and octadecylrhodamine (R18) as a fluorescence marker, and liposomes without fluorescence markers are used. The fluorescence of NBD ($\lambda$ex=470 nm; $\lambda$em=530 nm) is measured in the absence and presence of DNA/histidylated polylysine complexes at various pH values. The fusion of the liposomes induces a reduction in the fluorescence of NBD as a consequence of a reduction in the transfer energy between rhodamine and NBD.

These new complexes of nucleic acid and substituted polymer containing weakly basic groupings which can be protonated (cation) in a slightly acid medium in the presence of serum are more suitable for gene transfer in vivo than the DNA/polylysine or DNA/gluconylated polylysine complexes which are active only in the presence of auxiliaries such as chloroquine or fusiogenic and/or permeabilizing peptides.

The residues cause destabilization of cell membranes due to their property of being protonatable in an acid medium.

The residues which cause destabilization of cell membranes are proton captors which limit acidification of endosomes and, as a consequence, hinder fusion between late endosomes and liposomes. It should be noted that lysosomes are vesicles containing a large number of hydrolases and that these lysosomes are very effective in degrading biological macromolecules in general and nucleic acids in particular.

The term "weakly acid medium" means a medium of which the pH is less than that of plasma or serum, for example a pH of less than 7.4.

The term according to which the residues "are not active with respect to the recognition signal recognized by a cell membrane receptor" indicates that, on the one hand, to date there are no known receptors which are specific to these residues and, on the other hand, that these residues are not used as ligands.

A molecule or a molecular complex is active with respect to a recognition signal if it can be recognized selectively by a receptor, that is to say it plays the role of a ligand, an agonist or an antagonist.

Recognition signal recognized by a cell membrane receptor generally means a ligand (molecule or molecular complex) which is capable of being recognized selectively by the said receptor (ligand-receptor affinity$\geq 10^3$ l/mole).

The invention particularly relates to a complex between at least one (negatively charged) nucleic acid and at least one positively charged polymeric conjugate, the bond between the nucleic acid and the polymeric conjugate being electrostatic in nature and the polymeric conjugate containing a polymer formed from monomer units carrying free $NH_3^+$ functions, and being such that:

the free $NH_3^+$ functions of the abovementioned monomer units are substituted in a ratio of at least 10%, advantageously about 15% to about 45%, in particular 35%, this ratio being determined, for example, by nuclear magnetic resonance, by residues which can be protonated in a weakly acid medium causing destabilization of cell membranes, in particular the membrane of endocytosis vesicles, and/or of endosomes in a weakly acid medium, the abovementioned residues also having the following properties:

they are bases of which the pK in an aqueous medium is less than 8, such that a proportion of greater than 50% of these bases bonded to a cationic polymer is not protonated in a neutral medium of pH 7.4, they carry a functional group which enables them to be bonded to the abovementioned polymer, they are not active with respect to the recognition signal recognized by a cell membrane receptor, they can carry at least one free $NH_3^+$ function, it being possible for the free $NH_3^+$ functions of the abovementioned monomer units also to be substituted by non-charged residues causing a reduction in the positive charges with respect to the same unsubstituted polymeric conjugate, facilitating salting out of the nucleic acid in the course of dissociation of the complex, the abovementioned non-charged residues also having the following properties:

they carry at least one hydroxyl group, they are not active with respect to the recognition signal recognized by a cell membrane receptor, molecules constituting a recognition signal recognized by a cell membrane receptor optionally being present:

by substitution of some of the free $NH_3^+$ functions of the abovementioned monomer units (for example $\epsilon$-$NH_3^+$ of lysine), or on some of the abovementioned non-charged residues causing a reduction in the charge (for example gluconyl), and in particular on the hydroxyl groups of the abovementioned non-charged residues causing a reduction in charge, or on some of the abovementioned residues causing a destabilization of cell membranes (for example acetylimidazole), or by substitution of the optional free $NH_3^+$ function of the abovementioned residues causing a destabilization of cell membranes (for example histidine), with the proviso that all the free $NH_3^+$ functions make up at least 30% of the number of monomer units of the polymeric skeleton of the abovementioned polymeric conjugate.

The invention also relates to a complex between at least one (negatively charged) nucleic acid and at least one positively charged polymeric conjugate, the bond between the nucleic acid and the polymeric conjugate being electrostatic in nature and the polymeric conjugate containing a polymer formed from monomer units carrying free $NH_3^+$ functions, and being such that:

the free $NH_3^+$ functions of the abovementioned monomer units are substituted in a ratio of at least 10%, advantageously about 15% to about 45%, in particular 35%, this ratio being determined, for example, by nuclear magnetic resonance, by residues which can be protonated in a weakly acid medium causing destabilization of cell membranes, in particular the membrane of endocytosis vesicles, in a weakly acid medium, the abovementioned residues also having the following properties:

they belong to the family of compounds which carry an imidazole nucleus, they belong to the family of quinolines, they belong to the family of pterines, they belong to the family of pyridines, the abovementioned residues carry a functional group which enables them to be bonded to the abovementioned polymer, they can carry at least one free $NH_3^+$ function, they are not active with respect to the recognition signal recognized by a cell membrane receptor, it being possible for the free $NH_3^+$ functions of the abovementioned monomer units also to be substituted by at least one molecule which constitutes a recognition signal recognized by a cell membrane receptor, and/or by non-charged residues causing a reduction in the positive charges with respect to the same unsubstituted polymeric conjugate, facilitating salting out of the nucleic acid in the course of dissociation of the complex, with the proviso that all the abovementioned residues contain at least 30% of free $NH_3^+$ functions, it being possible for the free $NH_3^+$ functions of the abovementioned monomer units also to be substituted by at least one molecule which constitutes a recognition signal recognized by a cell membrane receptor, and/or by non-charged residues causing a reduction in the positive charges with respect to the same unsubstituted polymeric conjugate, facilitating salting out of the nucleic acid by dissociation of the complex, the abovementioned non-charged residues also having the following properties:

they carry at least one hydroxyl group, they are not active with respect to the recognition signal recognized by a cell membrane receptor, molecules constituting a recognition signal recognized by a cell membrane receptor optionally being present:

by substitution of some of the free $NH_3^+$ functions of the abovementioned monomer units (for example $\epsilon$-$NH_3^+$ of lysine), or on some of the abovementioned non-charged residues causing a reduction in the charge (for example gluconyl), and in particular on the hydroxyl groups of the abovementioned non-charged residues causing a reduction in charge, or on some of the abovementioned residues causing a destabilization of cell membranes (for example acetylimidazole), or by substitution of the optional free $NH_3^+$ function of the abovementioned residues causing a destabilization of cell membranes (for example histidine), with the proviso that all the free $NH_3^+$ functions make up at least 30% of the number of monomer units of the polymeric skeleton of the abovementioned polymeric conjugate.

The recognition signals can also cause a reduction in the positive charges of the polymeric conjugate if they are themselves neutral or acid and they are bonded to the polymer by substitution of an $NH_3^+$ function causing the loss of the + charge.

The recognition signals are molecules of low molecular weight (<5,000 daltons).

The number of molecules of the recognition signal bonded to the modified polymer can be:

for a signal molecule of very high affinity with respect to its receptor ($Ka>10^7$ l/mole), about 0.5 to 5, advantageously 1 molecule for about 10,000 monomer units of the substituted polymer, that is to say 1 molecule for about 50 molecules of the substituted polymer;

for a signal molecule of high affinity with respect to its receptor (Ka between $10^5$ l/mole and $10^7$ l/mole), about 0.5 to about 10, advantageously 1 molecule for about 200 monomer units of the substituted polymer, that is to say 1 molecule for about 1 molecule of substituted polymer;

for a signal molecule of moderate affinity with respect to its receptor ($Ka<10^5$ l/mole), about 10 to about 100, advantageously 50 molecules for about 200 monomer units of the substituted polymer, that is to say 50 molecules for about 1 molecule of substituted polymer.

The family of quinolines is represented by the following formula:

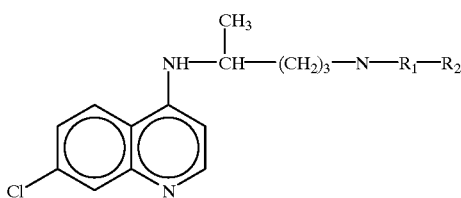

in which n has a value from 1 to 10, preferably 1 to 3.

The family of pterines is represented by the following formula:

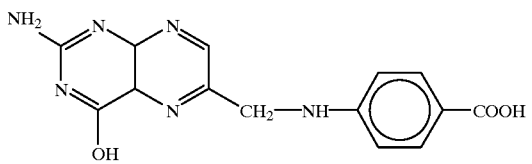

The family of pyridines is represented by the following formulae:

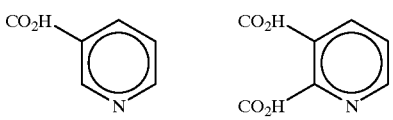

The invention also relates to a complex in which the residues causing destabilization of cell membranes in a weakly acid medium are
alkylimidazoles in which the alkyl radical contains 1 to 10, in particular 2 to 6 carbon atoms, and in which only one of the nitrogen atoms of the imidazole nucleus is substituted,
or quinolines of the formula:

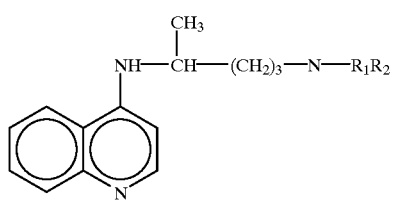

in which $R_1$ represents H and $R_2$ represents $(CH_2)_n$—$CO_2$—H, n being an integer varying from 1 to 10, and preferably having a value of 1 to 3.

The invention also relates to a complex in which the residues causing destabilization of cell membranes are chosen from: histidine, 4-carboxymethyl-imidazole, 3-(1-methyl-imidazol-4-yl)-alanine, 3-(3-methyl-imidazol-4-yl)-alanine, 2-carboxy-imidazole, histamine, 3-(imidazol-4-yl)-L-lactic acid, 2-(1-methyl-imidazol-4-yl)ethylamine, 2-(3 -methyl-imidazol-4-yl)ethylamine, β-alanyl-histidine-(carnosine), 7-chloro-4-(amino-1-methylbutylamino) quinoline, $N^4$-(7-chloro-4-quinolinyl)-1,4-pentanediamine, 8-(4-amino-1-methylbutylamino)-6-methoxyquinoline (primaquine), $N^4$-(6-methoxy-8-quinolinyl)-1,4-pentanediamine, quininic acid, quinolinecarboxylic acid, pteroic acid, nicotinic acid and quinolinic acid, in which the optional free $NH_3^+$ function of the abovementioned residues (for example histidine) can also be substituted by a molecule which constitutes a recognition signal recognized by a cell membrane receptor,
with the proviso that all the free $NH_3^+$ functions make up at least 30% of the number of monomer units of the polymeric skeleton of the abovementioned polymeric conjugate.

The invention relates to a complex between at least one (negatively charged) nucleic acid and at least one positively charged polymeric conjugate, the bond between the nucleic acid and the polymeric conjugate being electrostatic in nature and the polymeric conjugate containing a polymer formed from monomer units carrying free $NH_3^+$ functions, in particular residues of lysine or ornithine, and being such that:
the free $NH_3^+$ functions of the abovementioned monomer units are substituted in a ratio of at least 10%, advantageously about 15% to about 45%, in particular 35%, by residues causing a destabilization of cell membranes in a weakly acid medium,
the abovementioned residues also having the following properties:
they carry an imidazole nucleus,
they can carry at least one free $NH_3^+$ function,
they are not active with respect to the recognition signal,
the remaining free $NH_3^+$ functions of the abovementioned monomer units also being substituted to the extent of about 1% to about 60% by a molecule which constitutes a recognition signal recognized by a cell membrane receptor, this recognition signal having a molecular weight of less than 5,000, and it being possible for this recognition signal to be present in an amount of one molecule for about 200 units of polymeric conjugate or about 60 molecules for about 200 units of polymeric conjugate,
with the proviso that all the free $NH_3^+$ functions make up at least 30% of the number of monomer units of the polymeric skeleton of the abovementioned polymeric conjugate.

The term "not active with respect to the recognition signal" indicates that on the one hand to date there are no known receptors which are specific to these residues and, on the other hand, these residues are not used as ligands.

The invention also relates to a complex in which the polymer contains a polymeric grouping of the following formula (I):

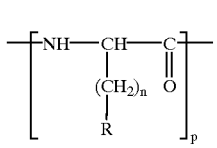

(I)

in which:
p is an integer varying from 15 to 900, preferably 100 to 300,
n is an integer varying from 1 to 6, and preferably has the value 4,
this polymeric grouping contains radicals R among which:
10% to 45% of the number of radicals R representing a residue carrying an imidazole nucleus and optionally a free $NH_3^+$ function, in particular a histidyl residue, it being possible for R to be represented by the formula:

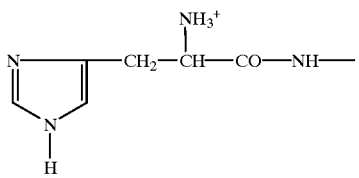

it being possible for the optional $NH_3^+$ function of the abovementioned residues also to be substituted by a molecule which constitutes a recognition signal, 10% to 90% of the number of radicals R representing free $\overline{\omega}$-amino $NH_3^+$ and optionally being substituted to the extent of 0 to 50% by a molecule which constitutes a recognition signal, in particular to the extent of 0 to 60, advantageously 1 molecule for about 200 units, or to the extent of 2 to 100, advantageously 50 molecules for about 200 units, and/or it also being possible for R to be made up to the extent of 0 to 45% of a group $NH-CO-(CHOH)_m-R_1$, in particular a dihydroxypropionylamido, erythronylamido, threonylamido, ribonylamido, arabinylamido, xylonylamido, lyxonylamido, gluconylamido, galactonylamido, mannonylamido, glycoheptonylamido or glycooctonylamido radical, m is an integer from 2 to 15, preferably 2 to 7, $R_1$ represents H or an alkyl radical having 1 to 15 carbon atoms, in particular $CH_3$, it being possible for these radicals to be substituted by a molecule which constitutes a recognition signal, with the proviso that all the free $NH_3^+$ functions make up at least 30% of the number of monomer units of the polymeric skeleton of the abovementioned polymeric conjugate.

In this class of complexes of the invention, the polymer is polylysine or polyornithine.

As shown by the examples, HepG2 (human hepatocarcinoma) cells are transfected effectively by polylysine substituted by 70 histidyl residues.

Polylysine substituted by 30±10% histidine has allowed transfection of various cells (human and murine) with a high efficiency, modulated according to the cell type and the promoter used.

The invention also relates to a complex in which the polymer comprises a polymeric grouping of the following formula (II):

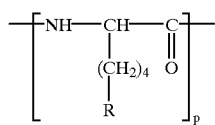

in which:

p has the meanings indicated above,

10% to 45% of the number of radicals R represent a residue carrying an imidazole nucleus and optionally a free $NH_3^+$ function, in particular a histidyl residue, it being possible for R to be represented by the formula

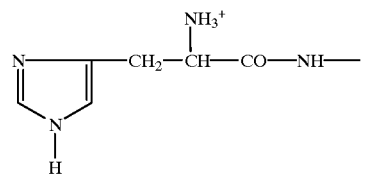

it being possible for the $NH_3^+$ functions of the abovementioned residues also to be substituted by a molecule which constitutes a recognition signal, the remainder of the radicals, that is to say 30% to 90% of the number of radicals R, representing $\overline{\omega}$-amino $NH_3^+$, and it being possible for 0 to 45% of the radicals R to be substituted by a molecule which constitutes a recognition signal recognized by a cell membrane receptor, with the proviso that all the free $NH_3^+$ functions make up at least 30% of the number of monomer units of the polymeric skeleton of the abovementioned polymeric conjugate.

The invention also relates to a complex, which is characterized in that the recognition signal is chosen from:

A)—simple or complex osides recognized by membrane lectins and chosen from:

a. Asialo-oligoside of the type of triantennar lactosamine: asialoglycoprotein receptor

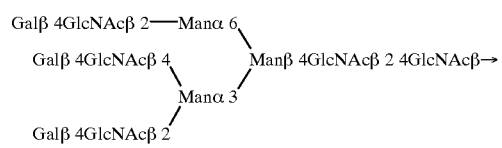

b. Asialo-oligoside of the type of tetraantennar lactosamine: asialoglycoprotein receptor

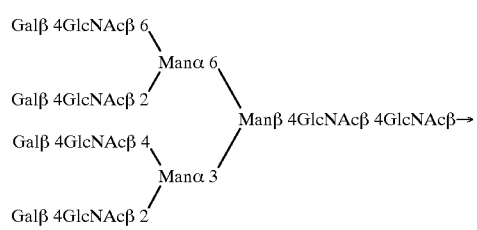

c. Lewis x: LECAM 2/3

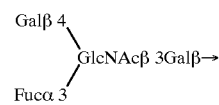

d. Lewis x sialyl: LECAM 3/2

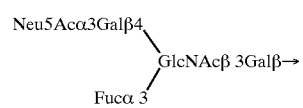

e. Sulphated Lewis x derivative (HNK1): LECAM 1

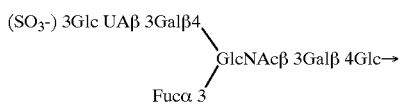

f. Oligomannoside: mannose receptor

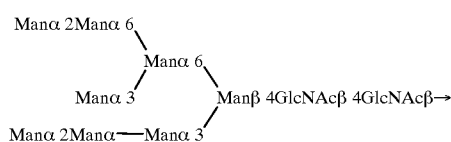

g. Phosphorylated oligomannoside: mannose 6-phosphate receptor

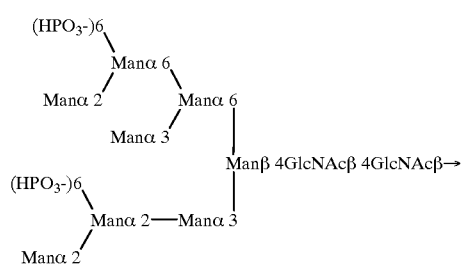

h. Oligosaccharide of the type of sulphated lactosamine: sulphated GaINAc 4 receptor

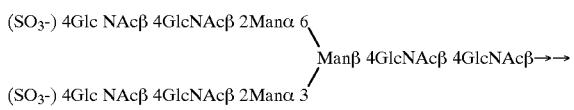

B) Peptides
a. anti-inflammatory peptides or certain of their fragments recognized by receptors of the vascular wall, such as
vasodilator intestinal polypeptide (VIP)
HSDAVFTDNYTRLRKQMAVKKYLNSILN-NH$_2$ (SEQ ID NO:2)
atrial natriuretic polypeptide (ANP)
SLRRSSCFGGRMDRIGAQSGLGCNSFRY (SEQ ID NO:3)
lipocortin
HDMNKVLDL (SEQ ID NO:4)
bradykinin
RPPGFSPFR (SEQ ID NO:5);
b. ligand peptides of integrins, such as peptides containing the sequence RGD, fibronectin ligand;
c. chemiotactic factors, such as formyl-peptides and their antagonists: FMLP, (N-formyl-Met-Leu-Phe);
d. peptide hormones, such as α-MSH:
Ac-SYSMEHFRWGKPV-NH$_2$ (SEQ ID NO:6) and their antagonists.
C) Natural metabolites, such as:
biotin,
carnitine,
tetrahydrofolate and folic acid, which can be both a recognition signal with respect to certain cells having suitable receptors and a destabilizer of cell membranes.

The invention also relates to a complex, which is characterized in that the nucleic acid can be chosen from:
a) marker genes, such as
genes containing luciferase,
green protein of the jellyfish *Aequarea Victoria*,
genes containing β-galactosidase,
genes containing chloramphenicol acetyltransferase,
genes which confer resistance to an antibiotic, such as hygromycin, neomycin etc . . . ;
b) genes with a therapeutic purpose, such as
receptors of lipoproteins of low-density, which are deficient in cases of hypercholesterolaemia,
coagulation factors: factors VIII and IX,
phenylalanine hydroxylase (phenylketonuria),
adenosine deaminase (ADA immunodeficiency),
lysosomal enzymes, such as β-glucosidase in the case of Gaucher's disease,
dystrophin and minidistriphin (myopathy),
tyrosine hydroxylase (Parkinson),
neurone growth factors (Alzheimer),
CFTR cystic fibrosis transmembrane conductance regulator (cystic fibrosis),
alpha-1-antitrypsin,
cytokines (interleukins, TNF tumour necrosing factor),
thymidine kinase of the Herpes simplex virus,
proteins of MHC, major histocompatibility complex, in particular HLA-B7,
cytosine deaminase,
genes which code for sense and antisense RNAs,
genes which code for ribozymes,
c) genes for the purpose of vaccines
genes which code for viral antigens (vaccination), for example: the gene which codes for the nucleoprotein of the influenza virus.

The invention also relates to a complex in which:
the polymer, in particular polylysine, has a degree of polymerization of about 15 to about 900, preferably 200,
the free NH$_3^+$ functions of the lysine units being substituted in a ratio of 35% by histidyl residues and optionally by a molecule which constitutes a recognition signal for 1 to 50 residues of lysine, where the said signal molecule has an affinity of at least $10^5$ l mole$^{-1}$ with respect to the receptor of the cell which the complex is to target, or optionally by 20 to 100 molecules of recognition signal for 200 lysine residues, where the said signal molecule has an affinity of less than $10^5$ l mole$^{-1}$ with respect to the said receptor,
the nucleic acid has a molecular weight of about $10^6$ to about $10^8$, in particular $3.10^6$ to $30.10^6$,
the ratio between the average number of base pairs of the nucleic acid per molecule of monomer unit, in particular lysine, is about 0.2 to about 6, preferably about 0.4 to about 0.6.
With regard to the affinities:
for a signal molecule of very high affinity with respect to its receptor (Ka>$10^7$ l/mole), about 0.5 to 5, advantageously 1 molecule for about 10,000 monomer units of the substituted polymer, that is to say 1 molecule for about 50 molecules of substituted polymer;
for a signal molecule of high affinity with respect to its receptor (Ka between $10^5$ l/mole and $10^7$ l/mole), about 0.5 to about 10, advantageously 1 molecule for about 200 monomer units of the substituted polymer, that is to say 1 molecule for about 1 molecule of substituted polymer;

for a signal molecule of moderate affinity with respect to its receptor (Ka<$10^5$ l/mole), about 10 to about 100, advantageously 50 molecules for about 200 monomer units of the substituted polymer, that is to say 50 molecules for about 1 molecule of substituted polymer.

The invention also relates to a positively charged polymeric conjugate containing units carrying free $NH_3^+$ functions and being such that:

the free $NH_3^+$ functions of the abovementioned monomer units are substituted in a ratio of at least 10%, advantageously about 15% to about 45%, in particular 35%, this ratio being determined, for example, by nuclear magnetic resonance, by residues which can be protonated in a weakly acid medium causing destabilization of cell membranes, in particular the membrane of endocytosis vesicles, in a weakly acid medium, the abovementioned residues also having the following properties:
they carry a functional group which enables them to be bonded to the abovementioned polymer,
they are not active with respect to the recognition signal recognized by a cell membrane receptor,
they can carry at least one free $NH_3^+$ function, it being possible for the free $NH_3^+$ functions of the abovementioned monomer units also to be substituted by non-charged residues causing a reduction in the positive charges with respect to the same unsubstituted polymeric conjugate, facilitating salting out of the nucleic acid by dissociation of the complex, the abovementioned non-charged residues also having the following properties:
they carry at least one hydroxyl group,
they are not active with respect to the recognition signal recognized by a cell membrane receptor,
it being possible for the hydroxyl groups of the abovementioned non-charged residues to be substituted by at least one molecule which constitutes a recognition signal recognized by a cell membrane receptor, molecules constituting a recognition signal recognized by a cell membrane receptor optionally being present:
by substitution of some of the free $NH_3^+$ functions of the abovementioned monomer units (for example $\epsilon$-$NH_3^+$ of lysines), or
on some of the abovementioned non-charged residues causing a reduction in the charge (for example gluconyl), and in particular on the hydroxyl groups of the abovementioned non-charged residues causing a reduction in charge, or
on some of the abovementioned residues causing a destabilization of cell membranes (for example acetylimidazole), or
by substitution of the optional free $NH_3^+$ function of the abovementioned residues causing a destabilization of cell membranes (for example histidine), with the proviso that all the free $NH_3^+$ functions make up at least 30% of the number of monomer units of the polymeric skeleton of the abovementioned polymeric conjugate.

The invention also relates to a polymeric conjugate as defined above or containing a polymeric grouping as defined above.

According to an advantageous embodiment of the invention, the polymeric conjugate is chosen from histidylated polylysine substituted by lactose, histidylated polylysine substituted by a complex oligoside such as Lewis[b], histidylated polylysine substituted by the peptide ANP, or histidylated polylysine substituted by biotin.

The polymeric conjugates of the invention can be prepared by one of the methods described in the following tables:

Table I: Methods for preparation of polymeric conjugates with recognition signals bonded to certain monomeric units of the polymer.

The respective order of introduction of residues responsible for destabilization, those responsible for the reduction in charge and recognition signals on to the polymer has been

| | POLYMER | | |
|---|---|---|---|
| Method | residues responsible for destabilization | residues responsible for the reduction in charge | recognition signal |
| I | 1 | — | 2 |
| II | 2 | — | 1 |
| III | 1 | 2 | 3 |
| IV | 1 | 3 | 2 |
| V | 2 | 1 | 3 |
| VI | 3 | 1 | 2 |
| VII | 2 | 3 | 1 |
| VIII | 3 | 2 | 1 |

Table II: Methods for preparation of polymeric conjugates with recognition signals bonded to certain residues responsible for destabilization of membranes.

The respective order of introduction of residues responsible for destabilization, those responsible for the reduction in charge and recognition signals on to the polymer has been indicated by 1, 2 and 3.

| | POLYMER | | |
|---|---|---|---|
| Method | residues responsible for destabilization | residues responsible for the reduction in charge | recognition signal |
| IX | 1 | — | 2 |
| X | 1 | 2 | 3 |
| XI | 1 | 3 | 2 |
| XII | 2 | 1 | 3 |

Table III: Methods for preparation of polymeric conjugates with recognition signals bonded to certain residues responsible for the reduction in charge.

The respective order of introduction of residues responsible for destabilization, those responsible for the reduction in charge and recognition signals on to the polymer has been indicated by 1, 2 and 3.

| | POLYMER | | |
|---|---|---|---|
| Method | residues responsible for destabilization | residues responsible for the reduction in charge | recognition signal |
| XII | 2 | 1 | 3 |
| XIV | 3 | 1 | 2 |
| XV | 1 | 2 | 3 |

The residues responsible for destabilization of membranes are chosen from: histidine, 4-carboxymethylimidazole, 3-(1-methyl-imidazol-4-yl)-alanine, 3-(I-methyl-imidazol-4-yl)-alanine, 2-carboxy-imidazole, histamine, 3-(imidazol-4-yl)-L-lactic acid, 2-(1-methyl-imidazol-4-yl)-ethylamine, 2-(3-methyl-imidazol-4-yl)-ethylamine, β-alanyl-histidine, 7-chloro-4-(amino-1-methylbutylamino)-quinoline, $N^4$-(7-chloro-4-quinolinyl)-1,4-pentanediamine, 8-(4-amino-1-methylbutylamino)-6-methoxy-quinoline, $N^4$-(6-methoxy-8-quinolinyl)-1,4-pentanediamine, quininic acid, quinolinecarboxylic acid, pteroic acid, nicotinic acid and quinolinic acid.

The residues responsible for the reduction in charge are chosen from: dihydroxypropionyl, erythronyl, threonyl, ribonyl, arabinyl, xylonyl, lyxonyl, gluconyl, galactonyl, mannonyl, glycoheptonyl, glycooctonyl.

The recognition signals are chosen from: osides, oligosides, peptides, metabolites, agonists and antagonists.

By way of example, the various methods of the tables are described:

I) The recognition signals are bonded to certain monomeric units of the polymer after introduction of the residues causing a destabilization of the cell membrane in the following manner:

A) Method I

Nicotinylated Polylysine a) Monomer units of the polymer carrying a free $NH_3^+$ function are partly substituted by residues causing destabilization of cell membranes. For example, polylysine (in particular in the p-toluenesulphonate form) is dissolved in an organic solvent (in particular dimethylsulphoxide) in the presence of a base (in particular diisopropylethylamine), molecules which cause destabilization of cell membranes (in particular nicotinic acid) and a coupling agent (in particular benzotriazolyl-N-oxytrisdimethylaminophosphonium hexafluorophosphate).

b) The recognition signals are bonded to certain ε-amino groupings of lysyl residues of the polymer.

By way of example of the bonding of recognition signals on to nicotinylated polylysine, the bonding of osides or oligosides is indicated below.

1) Bonding of Osides

Simple osides in the form of phenyl isothiocyanate derivatives are bonded to certain ε-amino functions of free lysyl residues of polylysine as described previously in Midoux et al., (Nucleic Acids Res. 1993 21: 871–878).

2) Bonding of Oligosides

Complex oligosides, such as bi-, tri- or tetra-antennar or Lewis asialo-oligosides are obtained in the form of phenyl isothiocyanate derivatives of glycopeptides by a method described in Monsigny et al., (French Patent 9407738, Monsigny M., Sdiqui N., Roche A. C. and Mayer R., 1994, Nouveaux dérivés d'oligosides, leur procédé de préparation et leurs applications [New oligoside derivatives, a process for their preparation and their uses]) and Sdiqui et al. (1995 New synthesis of glyco-amino acid conjugates, Carbohyd. Letters 1, 269–275). Glycopeptides in the form of phenyl isothiocyanate derivatives are bonded to certain ε-amino functions of free lysyl residues of polylysine as described previously in Midoux et al., (Nucleic Acids Res. 1993, 21: 871–878).

Histidylated Polylysine a) The monomer units of the polymer carrying a free $NH_3^+$ function are partly substituted by residues carrying a function which allows subsequent bonding of other molecules, such as those which will constitute a recognition signal, for example, after reaction in an organic medium with an N-hydroxysuccinimide ester of dithiopyridine-propionic acid or its derivatives.

b) The monomer units of the polymer carrying a free $NH_3^+$ function are then partly substituted by residues causing a destabilization of cell membranes, for example, after reaction in an organic medium with histidine, in which the $αNH_3^+$ group and the NH group of the imidazole nucleus are protected by tert-butyloxycarbonyl, in the presence of a coupling agent, such as benzotriazolyl-N-oxytrisdimethylaminophosphonium hexafluorophosphate. After reaction and purification, the amino functions of the histidyl residues of the polymer obtained are deprotected.

c) The recognition signals are bonded to dithiopyridyl groupings of the polymer.

By way of example of the bonding of recognition signals on to histidylated polylysine, the bonding of osides or oligosides is indicated below.

1) Bonding of Osides

Simple osides derived from glycopeptides with a dithiopyridyl function (pyroglutamyl-NH—$(CH_2)_2$—S—S-pyridine) by a method described in Monsigny et al., (French Patent 9407738, Monsigny M., Sdiqui N., Roche A. C. and Mayer R., 1994, Nouveaux dérivés d'oligosides, leur procédé de préparation et leurs applications [New derivatives of oligosides, a process for their preparation and their uses]) and Sdiqui et al., (1995 New synthesis of glyco-amino acid conjugates, Carbohyd. Letters 1:269–275) are reduced and bonded in an aqueous medium, buffered at a neutral pH, to dithiopyridyl functions of the polymer.

2) Bonding of Oligosides

Complex oligosides, such as bi-, tri- or tetra-antennar or Lewis asialo-oligosides derived from glycopeptides with a dithiopyridyl function (pyroglutamyl-NH—$(CH_2)_2$—S—S-pyridine) by a method described in Monsigny et al., (French Patent 9407738, Monsigny M., Sdiqui N., Roche A. C. and Mayer R., 1994, Nouveaux dérivés d'oligosides, leur procédé de préparation et leurs applications [New derivatives of oligosides, a process for their preparation and their uses]) and Sdiqui et al., (1995 New synthesis of glyco-amino acid conjugates, Carbohyd. Letters 1:269–275) are reduced and bonded in an aqueous medium, buffered at a neutral pH, to dithiopyridyl functions of the polymer.

B) Method III

Nicotinylated and Gluconylated Polylysine a) The monomer units of the polymer carrying a free $NH_3^+$ function are partly substituted by residues causing destabilization of cell membranes. For example, gluconylated polylysine is dissolved in an organic solvent (in particular dimethylsulphoxide) in the presence of a base (in particular diisopropylethylamine), molecules which cause destabilization of cell membranes (in particular nicotinic acid) and a coupling agent (in particular benzotriazolyl-N-oxytrisdimethylaminophosphonium hexafluorophosphate).

b) The monomer units of the polymer carrying an $NH_3^+$ function which is still free are then partly substituted by non-charged residues causing a reduction in charge. As regards bonding of residues causing the reduction in charge, for example, a polylysine salt (in particular in the form of the p-toluenesulphonate) is dissolved in an organic solvent (in particular dimethylsulphoxide) in the presence of a base (in particular diisopropylethylamine) and an activated hydroxylated organic acid (in particular δ-gluconolactone).

c) The recognition signals are bonded to certain ε-amino groupings of the lysyl residues of the polymer.

By way of example of the bonding of recognition signals on to histidylated polylysine, the bonding of osides or oligosides is indicated below.

1) Bonding of Osides

Simple osides in the form of phenyl isothiocyanate derivatives are bonded to certain ε-amino functions of free lysyl residues of polylysine as described previously in Midoux et al., (Nucleic Acids Res. 1993 21: 871–878).

2) Bonding of Oligosides

Complex oligosides, such as bi-, tri- or tetra-antennar or Lewis asialo-oligosides are obtained in the form of phenyl isothiocyanate derivatives of glycopeptides by a method described in Monsigny et al. (French Patent 9407738, Monsigny M., Sdiqui N., Roche A. C. and Mayer R., 1994, Nouveaux dérivés d'oligosides, leur procédé de préparation et leurs applications [New oligoside derivatives, a process for their preparation and their uses]) and Sdiqui et al (1995 New synthesis of glyco-amino acid conjugates. Carbohyd. Letters 1:69–275). Glycopeptides in the form of phenyl isothiocyanate derivatives are bonded to certain ε-amino functions of free lysyl residues of polylysine as described previously in Midoux et al., (Nucleic Acids Res. 1993, 21:871–878).

C) Method V

Gluconylated and Histidylated Polylysine a) The monomer units of the polymer carrying a free $NH_3^+$ function are partly substituted by residues carrying a function which allows subsequent bonding of other molecules. As regards the bonding of recognition signals, for example, a polylysine salt (in particular in the form of the p-toluenesulphonate) is dissolved in an organic solvent (in particular dimethylsulphoxide) in the presence of a base (in particular diisopropylethylamine) and the N-hydroxysuccinimide ester of dithiopyridine-propionic acid or its derivatives.

b) The monomer units of the polymer carrying an $NH_3^+$ function which is still free are then partly substituted by non-charged residues causing a reduction in charge. As regards the bonding of residues causing the reduction in charge, for example, a polylysine salt (in particular in the form of the p-toluenesulphonate) is dissolved in an organic solvent (in particular dimethylsulphoxide) in the presence of a base (in particular diisopropylethylamine) and an activated hydroxylated organic acid (in particular δ-gluconolactone).

c) The monomer units of the polymer carrying an $NH_3^+$ function which is still free are then partly substituted by residues causing a destabilization of cell membranes. As regards the bonding of residues causing a destabilization of cell membranes, for example, a polylysine salt (in particular in the form of the p-toluenesulphonate) is dissolved in an organic solvent (in particular dimethylsulphoxide) in the presence of a base (in particular diisopropylethylamine), molecules which cause a destabilization of cell membranes (in particular histidine in which the $\alpha NH_3^+$ group and the NH group of the imidazole nucleus are protected by tert-butyloxycarbonyl) and a coupling agent (in particular benzotriazolyl-N-oxytrisdimethylaminophosphonium hexafluorophosphate). After purification, the protected amino functions of the histidyl residues are deprotected.

d) The recognition signals are bonded to dithiopyridyl groupings of the polymer.

By way of example of the bonding of recognition signals on to histidylated polylysine, the bonding of osides or oligosides is indicated below.

1) Bonding of Osides

Simple osides derived from glycopeptides with a dithiopyridyl function (pyroglutamyl-NH—$(CH_2)_2$—S—S-pyridine) by a method described in Monsigny et al., (French Patent 9407738, Monsigny M., Sdiqui N., Roche A. C. and Mayer R., 1994, Nouveaux dérivés d'oligosides, leur procédé de préparation et leurs applications [New derivatives of oligosides, a process for their preparation and their uses]) and Sdiqui et al., (1995 New synthesis of glyco-amino acid conjugates, Carbohyd. Letters 1:269–275) are reduced and bonded in an aqueous medium, buffered at a neutral pH, to dithiopyridyl functions of the polymer.

2) Bonding of Oligosides

Complex oligosides, such as bi-, tri- or tetra-antennar or Lewis asialo-oligosides derived from glycopeptides with a dithiopyridyl function (pyroglutamyl-NH—$(CH_2)_2$—S—S-pyridine) by a method described in Monsigny et al., (French Patent 9407738, Monsigny M., Sdiqui N., Roche A. C. and Mayer R., 1994, Nouveaux dérivés d'oligosides, leur procédé de préparation et leurs applications [New derivatives of oligosides, a process for their preparation and their uses]) and Sdiqui et al., (1995 New synthesis of glyco-amino acid conjugates, Carbohyd. Letters 1:269–275) are reduced and bonded in an aqueous medium, buffered at a neutral pH, to dithiopyridyl functions of the polymer.

Gluconylated and Nicotinylated Polylysine a) The monomer units of the polymer carrying an $NH_3^+$ function which is still free are partly substituted by non-charged residues causing a reduction in charge. As regards the bonding of residues causing the reduction in charge, for example, a polylysine salt (in particular in the form of the p-toluenesulphonate) is dissolved in an organic solvent (in particular dimethylsulphoxide) in the presence of a base (in particular diisopropylethylamine) and an activated hydroxylated organic acid (in particular δ-gluconolactone).

b) The monomer units of the polymer carrying a free $NH_3^+$ function are then partly substituted by residues causing a destabilization of cell membranes. For example, gluconylated polylysine is dissolved in an organic solvent (in particular dimethylsulphoxide) in the presence of a base (in particular diisopropylethylamine), molecules which cause a destabilization of cell membranes (in particular nicotinic acid) and a coupling agent (in particular benzotriazolyl-N-oxytrisdimethylaminophosphonium hexafluorophosphate).

c) The recognition signals are bonded to certain ε-amino groupings of the lysyl residues of the polymer.

By way of example of the bonding of recognition signals on to histidylated polylysine, the bonding of osides or oligosides is indicated below.

1) Bonding of Osides

Simple osides in the form of phenyl isothiocyanate derivatives are bonded to certain ε-amino functions of free lysyl residues of polylysine as described previously in Midoux et al., (Nucleic Acids Res. 1993, 21:871–878).

2) Bonding of Oligosides

Complex oligosides, such as bi-, tri- or tetra-antennar or Lewis asialo-oligosides are obtained in the form of phenyl isothiocyanate derivatives of glycopeptides by a method described in Monsigny et al., (French Patent 9407738, Monsigny M., Sdiqui N., Roche A. C. and Mayer R., 1994, Nouveaux dérivés d'oligosides, leur procédé de préparation et leurs applications [New oligoside derivatives, a process for their preparation and their uses]) and Sdiqui et al., (1995 New synthesis of glyco-amino acid conjugates, Carbohyd. Letters 1:269–275). Glycopeptides in the form of phenyl isothiocyanate derivatives are bonded to certain ε-amino functions of free lysyl residues of polylysine as described previously in Midoux et al., (Nucleic Acids Res. 1993, 21: 871–878).

II) The recognition signals are bonded to certain monomeric units of the polymer before introduction of residues causing a destabilization of cell membranes, in the following manner:

A) Method II

Nicotinylated Polylysine

These substitutions follow any one of the protocols known to the person skilled in the art.

a) By way of example of the bonding of recognition signals on to polylysine (in particular in the form of the p-toluenesulphonate) dissolved in an organic solvent (in particular dimethylsulphoxide) in the presence of a base (in particular diisopropylethylamine), the bonding of osides and oligosides is indicated below.

1) Bonding of Osides

Simple osides in the form of phenyl isothiocyanate derivatives are bonded to certain ε-amino functions of free lysyl residues of polylysine as described previously in Midoux et al., (Nucleic Acids Res. 1993 21: 871–878).

2) Bonding of Oligosides

Complex oligosides, such as bi-, tri- or tetra-antennar or Lewis asialo-oligosides are obtained in the form of phenyl isothiocyanate derivatives of glycopeptides by a method described in Monsigny et al., (French Patent 9407738, Monsigny M., Sdiqui N., Roche A. C. and Mayer R., 1994, Nouveaux dérivés d'oligosides, leur procédé de préparation et leurs applications [New oligoside derivatives, a process for their preparation and their uses]) and Sdiqui et al. (1995 New synthesis of glyco-amino acid conjugates, Carbohyd. Letters 1, 269–275). Glycopeptides in the form of phenyl isothiocyanate derivatives are bonded to certain ε-amino functions of free lysyl residues of polylysine as described previously in Midoux et al., (Nucleic Acids Res. 1993, 21: 871–878).

b) As regards the bonding of residues which cause destabilization of membranes, for example, polylysine substituted by osides or oligosides is dissolved in an organic solvent (in particular dimethylsulphoxide) in the presence of a base (in particular diisopropylethylamine), molecules which cause a destabilization of cell membranes (in particular nicotinic acid) and a coupling agent (in particular benzotriazolyl-N-oxytrisdimethylaminophosphonium hexafluorophosphate).

B) Method VI

Gluconylated and Nicotinylated Polylysine

These substitutions follow any one of the protocols known to the person skilled in the art.

a) The monomer units of the polymer carrying an $NH_3^+$ function which is still free are partly substituted by non-charged residues causing a reduction in charge. As regards the bonding of residues causing the reduction in charge, for example, a polylysine salt (in particular in the form of the p-toluenesulphonate) is dissolved in an organic solvent (in particular dimethylsulphoxide) in the presence of a base (in particular diisopropylethylamine) and an activated hydroxylated organic acid (in particular δ-gluconolactone).

b) By way of example of the bonding of recognition signals on to the gluconylated polylysine dissolved in an organic solvent (in particular dimethylsulphoxide) in the presence of a base (in particular diisopropylethylamine), the bonding of osides or oligosides is indicated below.

1) Bonding of Osides

Simple osides in the form of phenyl isothiocyanate derivatives are bonded to certain ε-amino functions of free lysyl residues of polylysine as described previously in Midoux et al., (Nucleic Acids Res. 1993 21: 871–878).

2) Bonding of Oligosides

Complex oligosides, such as bi-, tri- or tetra-antennar or Lewis asialo-oligosides are obtained in the form of phenyl isothiocyanate derivatives of glycopeptides by a method described in Monsigny et al., (French Patent 9407738, Monsigny M., Sdiqui N., Roche A. C. and Mayer R., 1994, Nouveaux dérivés d'oligosides, leur procédé de préparation et leurs applications [New oligoside derivatives, a process for their preparation and their uses]) and Sdiqui et al. (1995 New synthesis of glyco-amino acid conjugates, Carbohyd. Letters 1:269–275). Glycopeptides in the form of phenyl isothiocyanate derivatives are bonded to certain ε-amino functions of free lysyl residues of polylysine as described previously in Midoux et al., (Nucleic Acids Res. 1993, 21: 871–878).

c) As regards the bonding of residues which cause destabilization of membranes, for example, polylysine substituted by osides or oligosides is dissolved in an organic solvent (in particular dimethylsulphoxide) in the presence of a base (in particular diisopropylethylamine), molecule which cause a destabilization of cell membranes (in particular nicotinic acid) and a coupling agent (in particular benzotriazolyl-N-oxytrisdimethylaminophosphonium hexafluorophosphate).

III) The recognition signals are bonded to certain destabilizing residues

A) Method IX

Histidylated Polylysine a) The monomer units of the polymer carrying a free $NH_3^+$ function are partly substituted by residues causing a destabilization of cell membranes. For example, after reaction in an organic medium with histidine, in which the $NH_3^+$ group and the NH group of the imidazole nucleus are protected by tert-butyloxycarbonyl, in the presence of a coupling agent, such as benzotriazolyl-N-oxytrisdimethylaminophosphonium hexafluorophosphate. After reaction and purification, the amino functions of the histidyl residues of the polymer obtained are deprotected.

b) The recognition signals are bonded to certain $NH_3^+$ groupings of the residues causing destabilization of membranes.

By way of example of the bonding of recognition signals on to the histidylated polylysine, the bonding of oligosides is indicated below.

Complex oligosides, such as the asialo-oligosides of the triantennar or tetraantennar or Lewis type, are obtained in the form of phenyl isothiocyanate derivatives of glycopeptides by a method described in Monsigny et al., (French Patent 9407738, Monsigny M., Sdiqui N., Roche A. C. and Mayer R., 1994, Nouveaux dérivés d'oligosides, leur procédé de préparation et leurs applications [New derivatives of oligosides, a process for their preparation and their uses]) and Sdiqui et al. (1995 New synthesis of glyco-amino acid conjugates, Carbohyd. Letters 1:269–275). The glycopeptides in the form of phenyl isothiocyanate derivatives are bonded in an aqueous medium, buffered at a neutral pH, to certain $NH_2$ functions of the histidyl residues. At this pH, bonding to the lysine $NH_3^+$ is very weak, or even impossible.

B) Method XII

Gluconylated and Histidylated Polylysine a) The monomer units of the polymer carrying a free $NH_3^+$ function are partly substituted by non-charged residues causing a reduction in charge. As regards the bonding of residues causing a reduction in charge, for example, a polylysine salt (in particular in the form of the p-toluenesulphonate) is dissolved in an organic solvent (in particular dimethylsulphoxide) in the presence of a base (in particular diisopropylethylamine) and an activated hydroxylated organic acid (in particular δ-gluconolactone).

b) the monomer units of the polymer carrying an $NH_3^+$ function which is still free are then partly substituted by residues causing a destabilization of cell membranes. As regards the bonding of residues causing a destabilization of cell membranes, for example, a polylysine salt (in particular in the form of the p-toluenesulphonate) is dissolved in an organic solvent (in particular dimethylsulphoxide) in the presence of a base (in particular diisopropylethylamine), molecules which cause a destabilization of cell membranes (in particular histidine, in which the αNH$_3^+$ group and the NH group of the imidazole nucleus are protected by tert-butyloxycarbonyl) and a coupling agent (in particular benzotriazolyl-N-oxytrisdimethylaminophosphonium hexafluorophosphate). After purification, the protected amino functions of the histidyl residues are deprotected.

c) The recognition signals are bonded to certain NH$_3^+$ groupings of residues causing a destabilization of membranes.

By way of example of the bonding of recognition signals on to histidylated polylysine, the bonding of oligosides is indicated below.

Complex oligosides, such as bi-, tri- or tetra-antennar or Lewis asialo-oligosides are obtained in the form of phenyl isothiocyanate derivatives of glycopeptides by a method described in Monsigny et al., (French Patent 9407738, Monsigny M., Sdiqui N., Roche A. C. and Mayer R., 1994, Nouveaux dérivés d'oligosides, leur procédé de préparation et leurs applications [New oligoside derivatives, a process for their preparation and their uses]) and Sdiqui et al. (1995 New synthesis of glyco-amino acid conjugates, Carbohyd. Letters 1:269–275). Glycopeptides in the form of phenyl isothiocyanate derivatives are bonded to certain $\alpha$NH functions of histidyl residues; at this pH, bonding to the lysine $NH_3^+$ is very weak or even impossible.

C) Method IX

Imidazolated Polylysine a) The monomer units of the polymer carrying a free $NH_3^+$ function are partly substituted by residues causing a destabilization of cell membranes. As regards the bonding of residues causing a destabilization of cell membranes, for example, a polylysine salt (in particular in the form of the p-toluenesulphonate) is dissolved in an organic solvent (in particular dimethylsulphoxide) in the presence of a base (in particular diisopropylethylamine), molecules which cause a destabilization of cell membranes (in particular 4-carboxymethyl-imidazole) and a coupling agent (in particular benzotriazolyl-N-oxytrisdimethylaminophosphonium hexafluorophosphate).

b) The recognition signals are bonded to certain imidazole nuclei of the residues causing a destabilization of membranes.

By way of example of the bonding of recognition signals to the imidazolated polylysine, the bonding of peptides or glycopeptides is indicated below.

The imidazole residues can easily be alkylated in a neutral medium by compounds which have an activated grouping, such as, for example, iodoacetamide or its derivatives; this is known from the works by Korman S. and Clarke H. T. in 1956 (J. Biol. Chem. 113:133). The alkylation of imidazoles by an iodoacetamide derivative is carried out at a pH close to neutrality, for example 7.0. At this pH, the $\epsilon$-amino groups of the lysine are not affected, but they would be at a much more alkaline pH of 9 or beyond. The recognition signals of a peptide or glycopeptide nature (Monsigny et al., French Patent 9407738, 1994, Nouveaux dérivés d'oligosides, leur procédé de préparation et leurs applications [New derivatives of oligosides, a process for their preparation and their uses] and Sdiqui et al, 1995 New synthesis of glyco-amino acid conjugates. Carbohyd. Letters 1:269–275) can easily be substituted by an iodoacetamide grouping. The derivatives of the type $ICH_2CONHR$: I—$CH_2$—CO—NH-peptide or I—$CH_2$—CO—NH-glycopeptide, are bonded in an aqueous medium, buffered at a neutral pH, to the 3-nitrogen, and with a lower efficiency to the 1-nitrogen, leading to stable N-carboxymethyl derivatives. It is also possible to use bromoacetamide derivatives, which are also excellent reagents for alkylation of imidazole residues (see, for example, Henrikson et al., 1965 J. Biol. Chem. 240:2921). This type of substitution, with the proviso of substitution of a small number of imidazole residues by recognition signals having a high affinity sufficient for their receptor, does not cause the polymer substituted by imidazole residues to lose its capacity for destabilizing membranes at a slightly acid pH.

IV) The recognition signals are bonded to certain neutralizing residues.

A) Method XIII

Gluconylated and Imidazolated Polylysine a) The monomer units of the polymer carrying a free $NH_3^+$ function are partly substituted by non-charged residues causing a reduction in charge. As regards the bonding of residues causing the reduction in charge, for example, a polylysine salt (in particular in the form of the p-toluenesulphonate) is dissolved in an organic solvent (in particular dimethylsulphoxide) in the presence of a base (in particular diisopropylethylamine) and two activated hydroxylated organic acids (in particular 6-deoxy-6-iodo-$\delta$-gluconolactone in one part and $\delta$-gluconolactone in 10 to 50 parts).

b) The monomer units of the polymer carrying a free $NH_3^+$ function are partly substituted by residues causing a destabilization of cell membranes. As regards the bonding of residues causing a destabilization of cell membranes, for example, a polylysine salt (in particular in the form of the p-toluenesulphonate) is dissolved in an organic solvent (in particular dimethylsulphoxide) in the presence of a base (in particular diisopropylethylamine), molecules which cause a destabilization of cell membranes (in particular 4-carboxymethyl-imidazole) and a coupling agent (in particular benzotriazolyl-N-oxytrisdimethylaminophosphonium hexafluorophosphate).

c) The recognition signals are bonded to certain neutralizing residues.

By way of example of the bonding of recognition signals on to the gluconylated and histidylated polylysine, the bonding of oligosides is indicated below.

Complex oligosides, such as the bi-, tri- or tetra-antennar or Lewis asialo-oligosides derived from glycopeptides with a dithiopyridyl function (pyroglutamyl-NH—$(CH_2)_2$—S—S-pyridine) by a method described in Monsigny et al., (French Patent 9407738, Monsigny M., Sdiqui N., Roche A. C. and Mayer R., 1994, Nouveaux dérivés d'oligosides, leur procédé de preparation at leurs applications [New derivatives of oligosides, a process for their preparation and their uses]) and Sdiqui et al., (1995 New synthesis of glyco-amino acid conjugates, Carbohyd. Letters 1:269–275) are reduced by triscarboxyethylphosphine in a neutral medium (pH about 7.0), for example, and bonded in an aqueous medium, buffered at a slightly alkaline pH (at about pH 8.5), to the 6-deoxy-6-iodo-gluconyl residues of the polymer. This type of substitution, with the proviso of substitution of a small number of imidazole residues by recognition signals having a high affinity for their receptor, does not cause the polymer substituted by imidazole residues to lose its capacity for destabilization of membranes at a slightly acid pH.

B) Method XIII

Gluconylated and Imidazolated Polylysine a) The monomer units of the polymer carrying a free $NH_3^+$ function are partly substituted by non-charged residues causing a reduction in charge. As regards the bonding of residues causing the reduction in charge, for example, a polylysine salt (in particular in the form of the p-toluenesulfonate is dissolved in an organic solvent (in particular dimethylsulphoxide) in the presence of a base (in particular diisopropylethylamine) and two activated hydroxylated organic acids (in particular 6-bromoacetamido-L-gulono-1,5-lactone in one part and δ-gluconolactone in 10 to 50 parts). 6-bromoacetamido-L-gulono-1,5-lactone is obtained after reduction by cyanoborohydride of the imine obtained by mixing an ammoniacal solution ($NH_4OH$ or $(NH_4)_2CO_3$) and a solution of a uronic acid, for example glucuronic acid, and then by acylation of the amine by an activated bromoacetate, for example bromoacetic anhydride or succinimidyl bromoacetate.

b) The monomer units of the polymer carrying a free $NH_3^+$ function are partly substituted by residues causing a destabilization of cell membranes. As regards the bonding of residues causing a destabilization of cell membranes, for example, a polylysine salt (in particular in the form of the p-toluenesulfonate) is dissolved in an organic solvent (in particular dimethylsulphoxide) in the presence of a base (in particular diisopropylethylamine), molecules which cause a destabilization of cell membranes (in particular 4-carboxymethyl-imidazole) and a coupling agent (in particular benzotriazolyl-N-oxytrisdimethylaminophosphonium hexafluorophosphate).

c) The recognition signals are bonded to certain neutralizing residues.

By way of example of the bonding of recognition signals on to the gluconylated and histidylated polylysine, the bonding of oligosides is indicated below.

Complex oligosides, such as the bi-, tri- or tetra-antennar or Lewis asialo-oligosides derived from glycopeptides with a dithiopyridyl function pyroglutamyl-NH—$(CH_2)_2$—S—S-pyridine) by a method described in Monsigny et al., (French Patent 9407738, Monsigny M., Sdiqui N., Roche A. C. and Mayer R., 1994, Nouveaux dérivés d'oligosides, leur procédé de preparation at leurs applications [New derivatives of oligosides, a process for their preparation and their uses]) and Sdiqui et al., (1995 New synthesis of glyco-amino acid conjugates, Carbohyd. Letters 1:269–275) are reduced by triscarboxyethylphosphine in a neutral medium (pH about 7.0), for example, and bonded in an aqueous medium, buffered at a slightly alkaline pH (at about pH 8.5), to the bromoacetamido-gluconyl residues of the polymer. This type of substitution, with the proviso of substitution of a small number of imidazole residues by recognition signals having a high affinity for their receptor, does not cause the polymer substituted by imidazole residues to lose its capacity for destabilization of membranes at a slightly acid pH.

The nucleic acid/polymeric conjugate complex is obtained by mixing a solution of the nucleic acid in question and a solution of the polymeric conjugate. The said solutions are preferably prepared from physiological serum or a buffer or a cytocompatible medium.

According to an advantageous embodiment of the invention, a complex as described above or a conjugate as described above is used for the in vitro, ex vivo or in vivo transfection of cells with the aid of a gene, in particular those defined previously.

According to an advantageous embodiment of the invention, a complex or a conjugate as described above is used, being characterized in that the cells are chosen from;
 cells of haematopoietic strains;
 dendritic cells;
 liver cells;
 skeletal muscle cells;
 skin cells:
 fibroblasts,
 keratinocytes,
 dendritic cells,
 melanocytes;
 cells of the vascular walls;
 endothelial;
 smooth muscle;
 epithelial cells of the respiratory tract;
 cells of the central nervous system;
 cancerous cells;
 cells of the immune system, such as lymphocytes, macrophages, NK cells etc.

According to an advantageous embodiment of the invention, the method of in vitro or ex vivo transfection is characterized in that a complex as described previously is brought into contact with a medium containing cells to be transfected under conditions such that there is:
 passage of the complex from the medium into the cytoplasm of the cells,
 salting out of the nucleic acid involved in the abovementioned complex in the cytosol and/or the nucleus of the cells,
 transcription and expression of the nucleic acid in the transfected cells,
 expression of the protein corresponding to the transfected gene.

The invention also relates to a pharmaceutical composition, which is characterized in that it comprises, as the active substance, at least one of the complexes as described above, or at least one of the conjugates as described above, in combination with a pharmaceutically acceptable vehicle.

According to an advantageous embodiment of the invention, a complex as described above or a conjugate as described above is used for the preparation of a medicament intended, for example, for treatment of congenital or acquired metabolic deficiency, or treatment of tumours, or for the preparation of a vaccine, for example a vaccine against influenza.

The invention also relates to a set or kit comprising:
 a polymeric conjugate as described above, such as polylysine substituted by a residue causing a destabilization of cell membranes in a weakly acid medium, this polymeric conjugate being capable of optionally carrying a recognition signal, which is or is not bonded beforehand to the abovementioned polymeric conjugate, the said recognition signal being a function of the cell to be targeted,
 optionally a plasmid containing at least one gene to be transferred, and optionally the system for regulation of the expression of the abovementioned gene,
 reagents which allow optional bonding of the recognition signal on to the abovementioned polymeric conjugate,
 reagents which allow the formation of a complex as described above, or between the polymeric conjugate and the gene to be transferred, or between the polymeric conjugate and a plasmid containing the gene to be transferred,
 reagents which allow transfection of the cell by the abovementioned complex.

Figure 1:
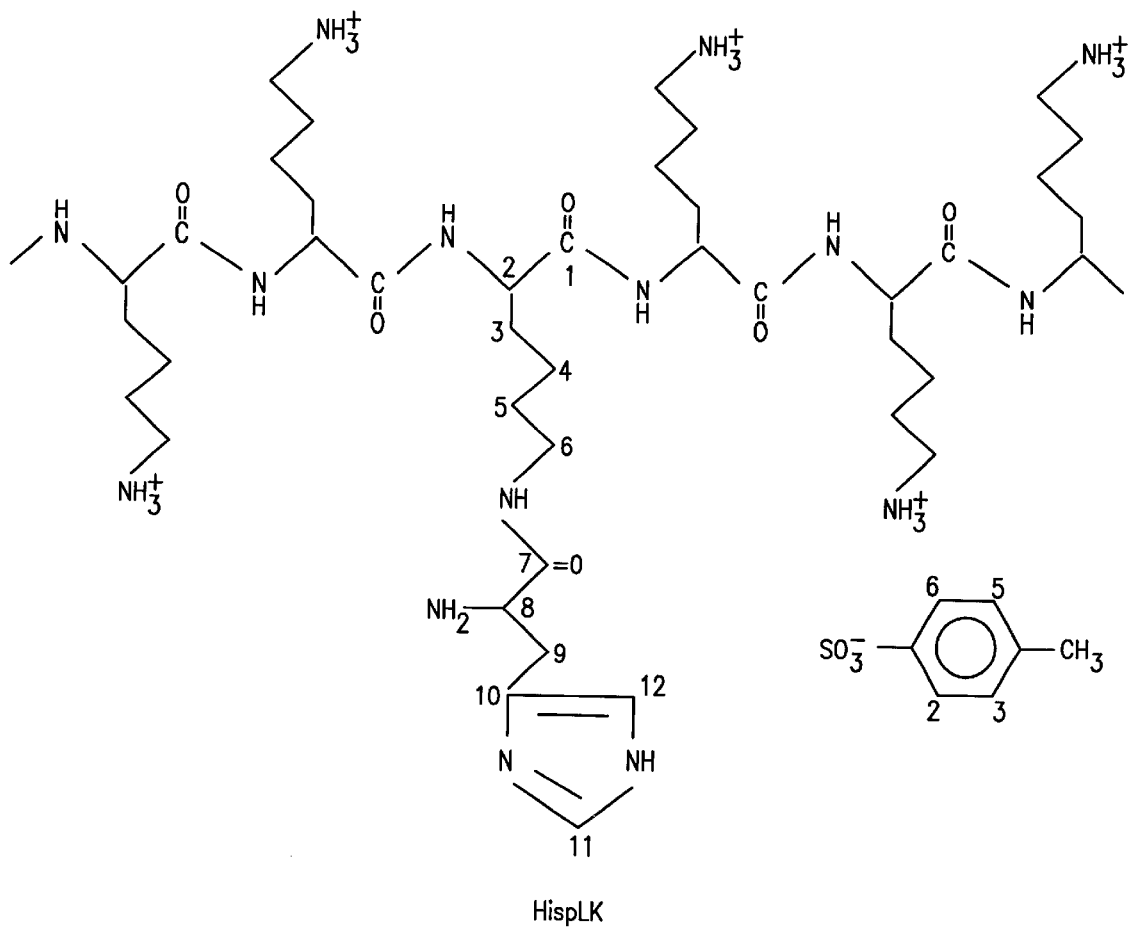
FIG. 1
Figure 2:
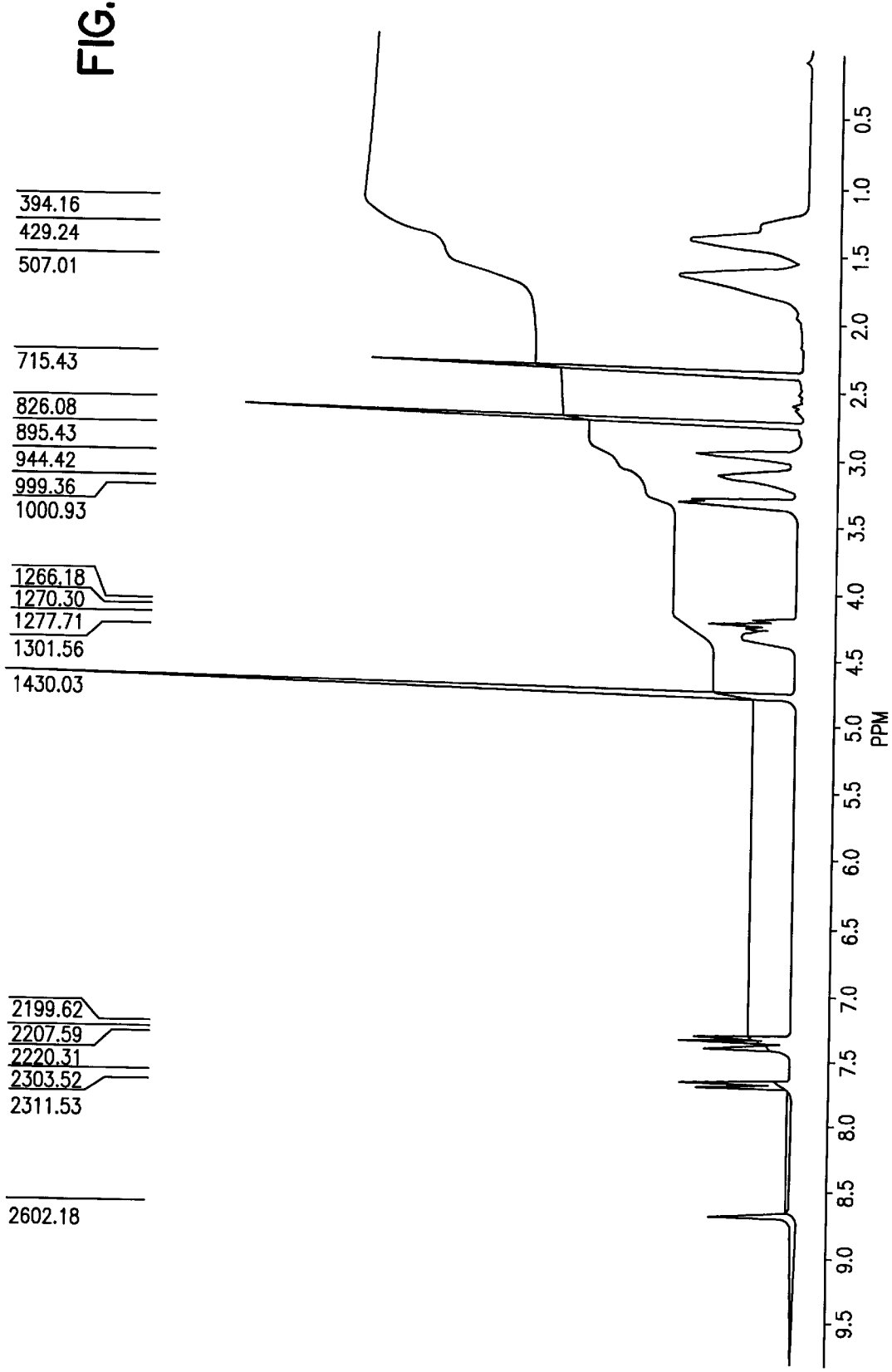
Figure 3:
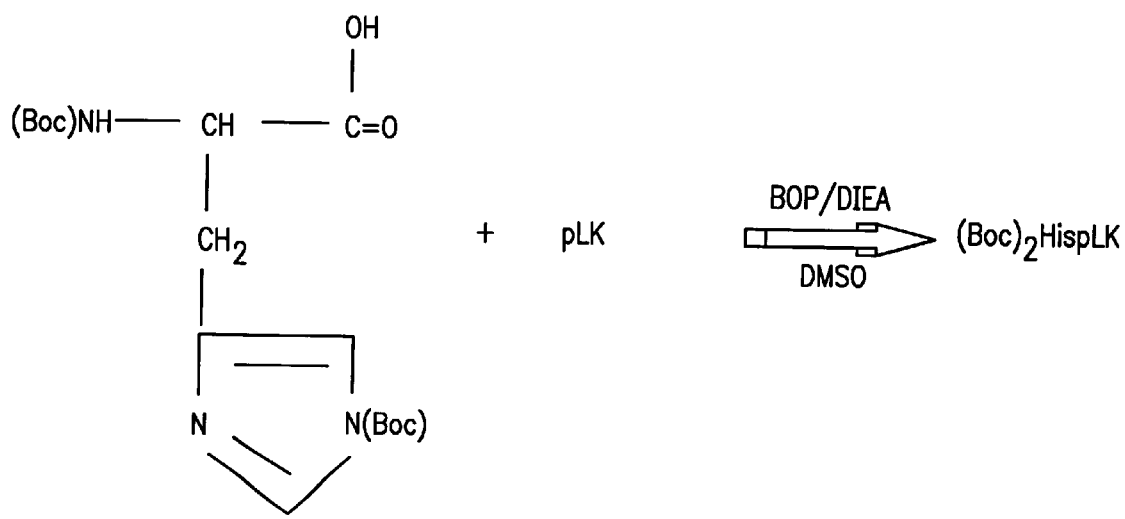
Figure 3:
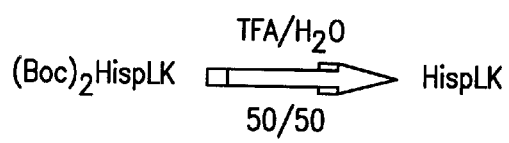
Figure 4:
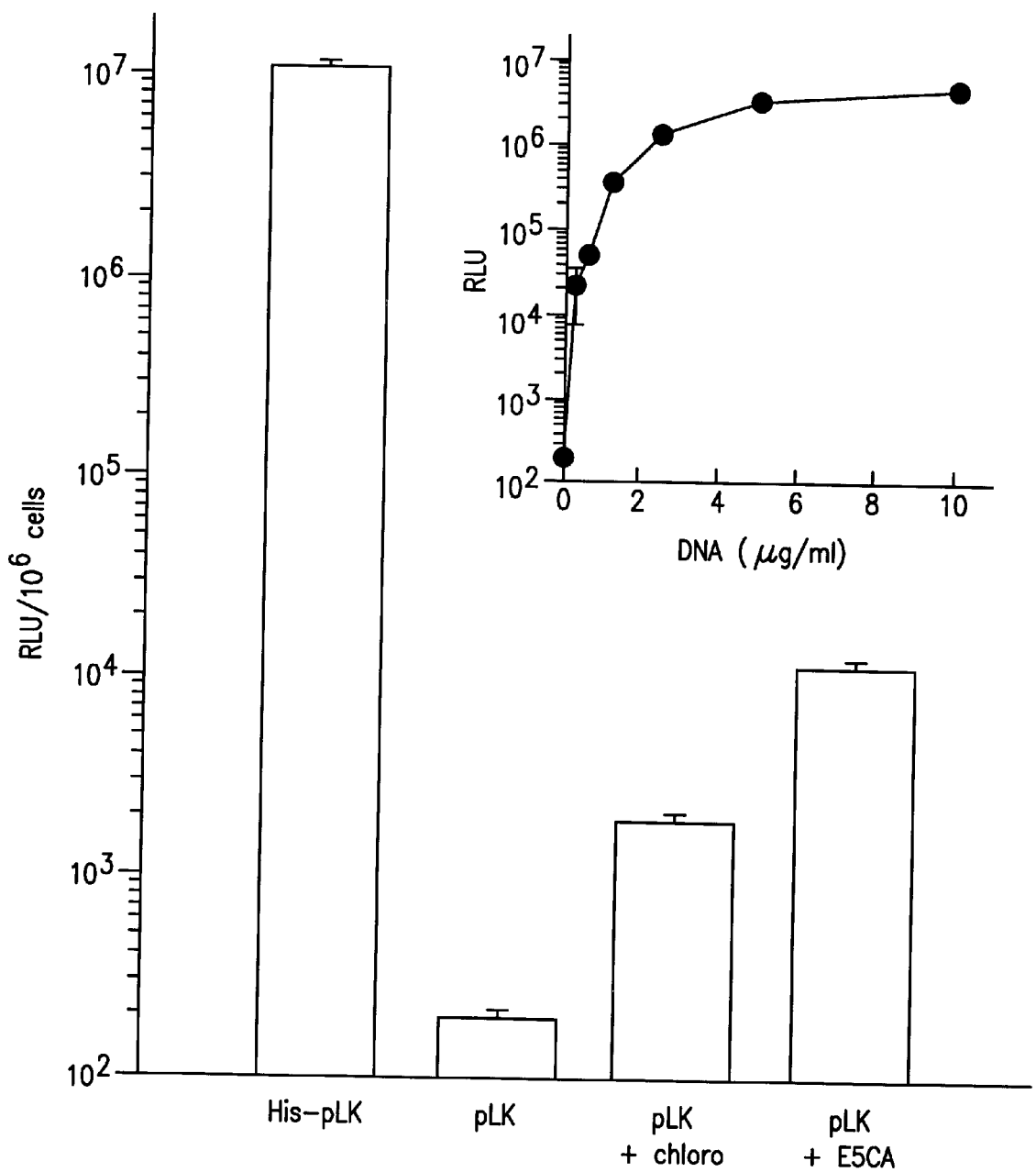
Figure 5:
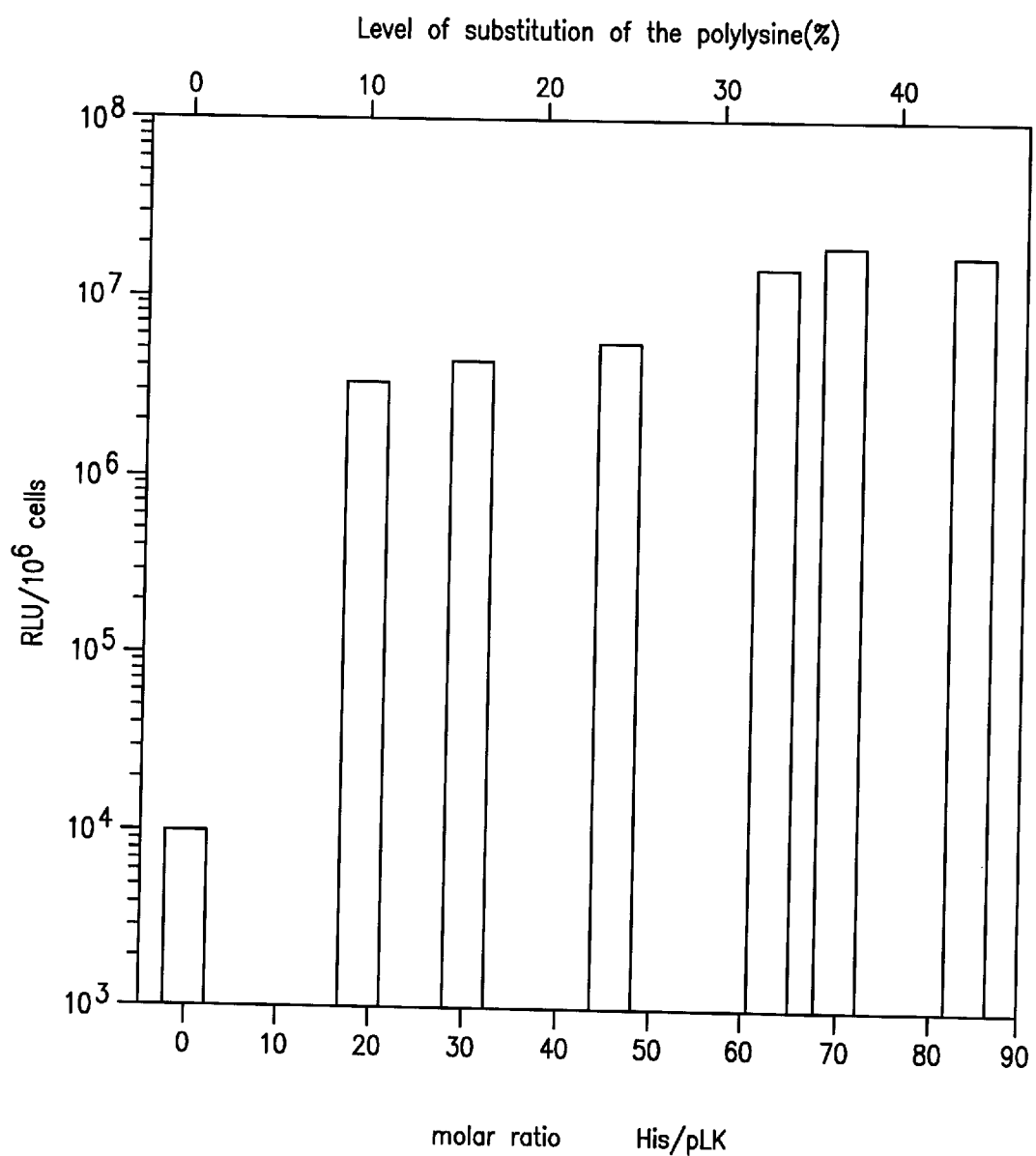
Figure 6:
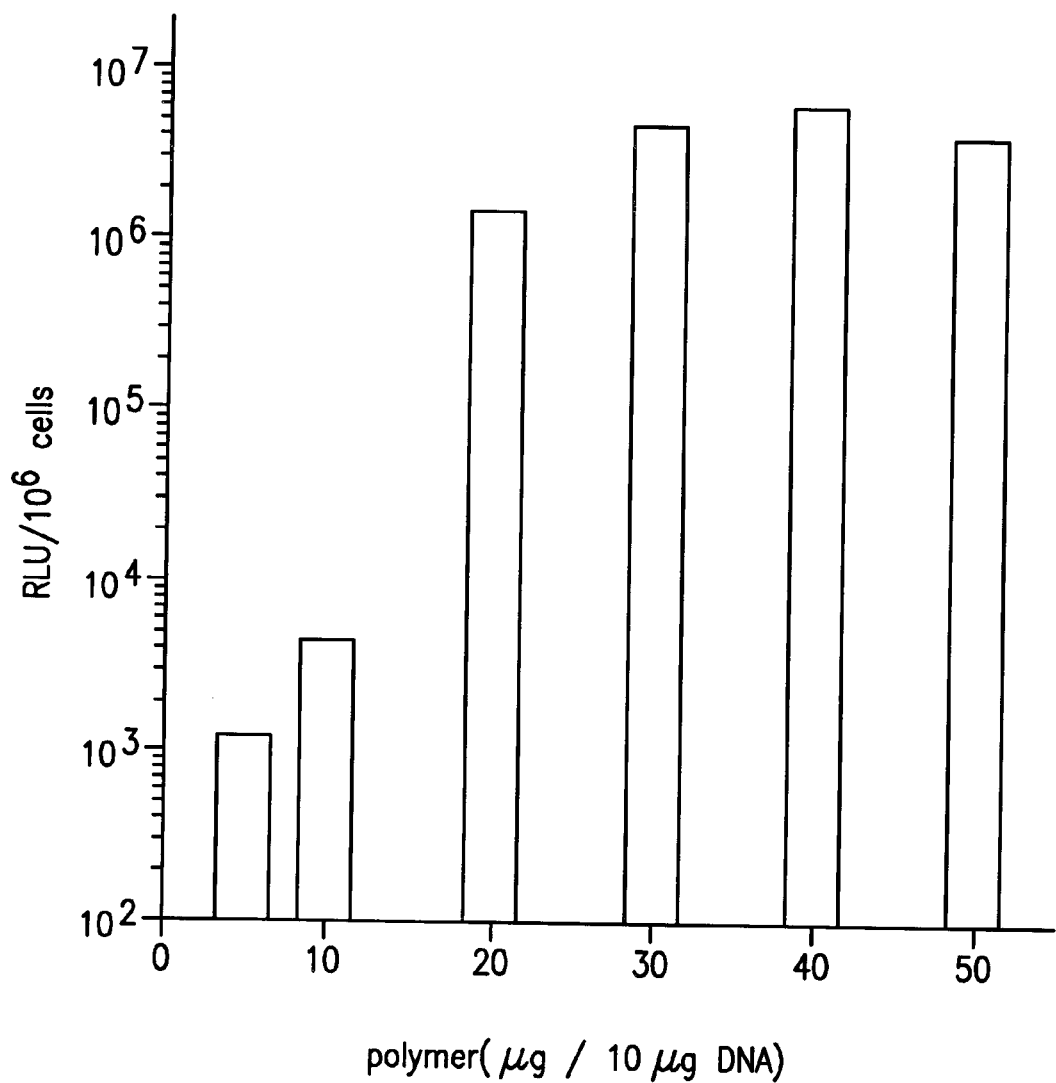
Figure 7:
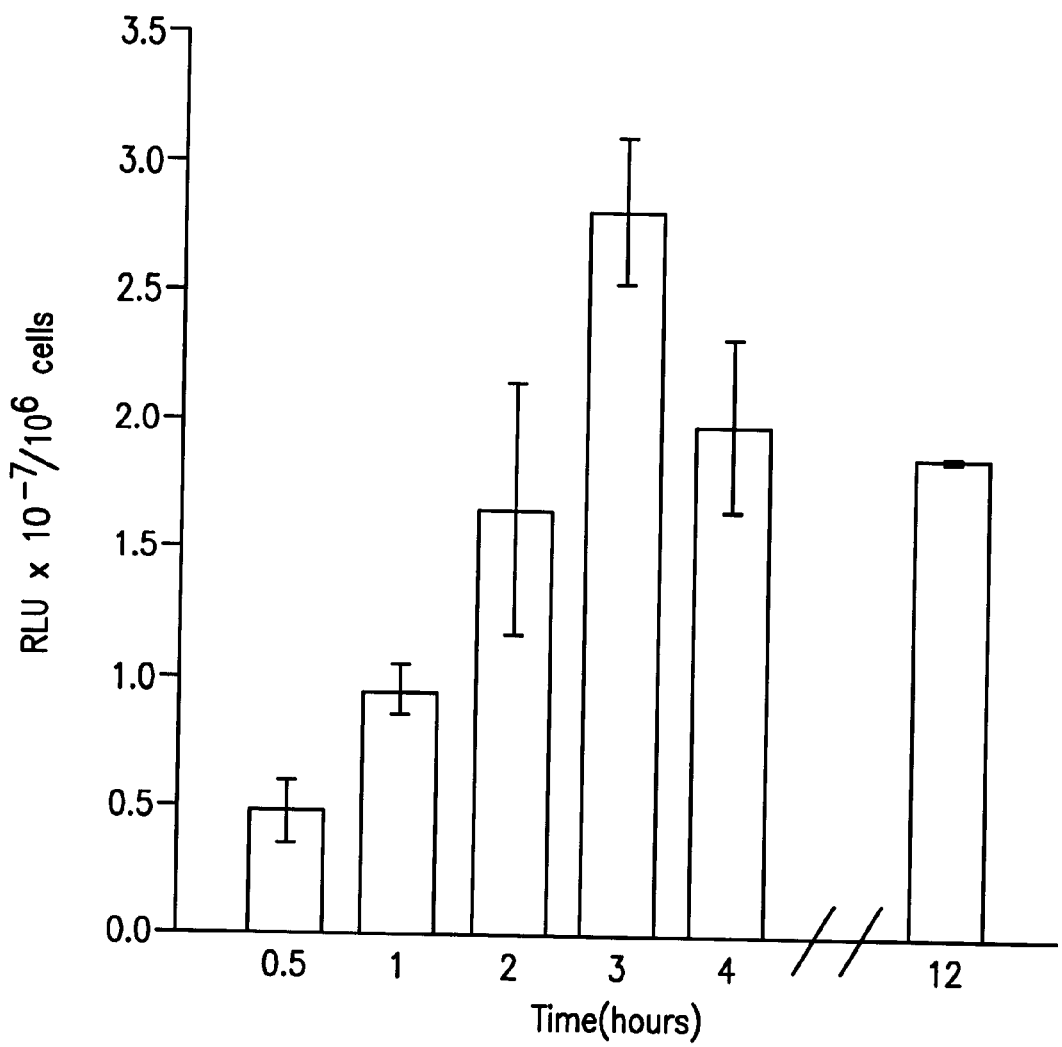
Figure 8:
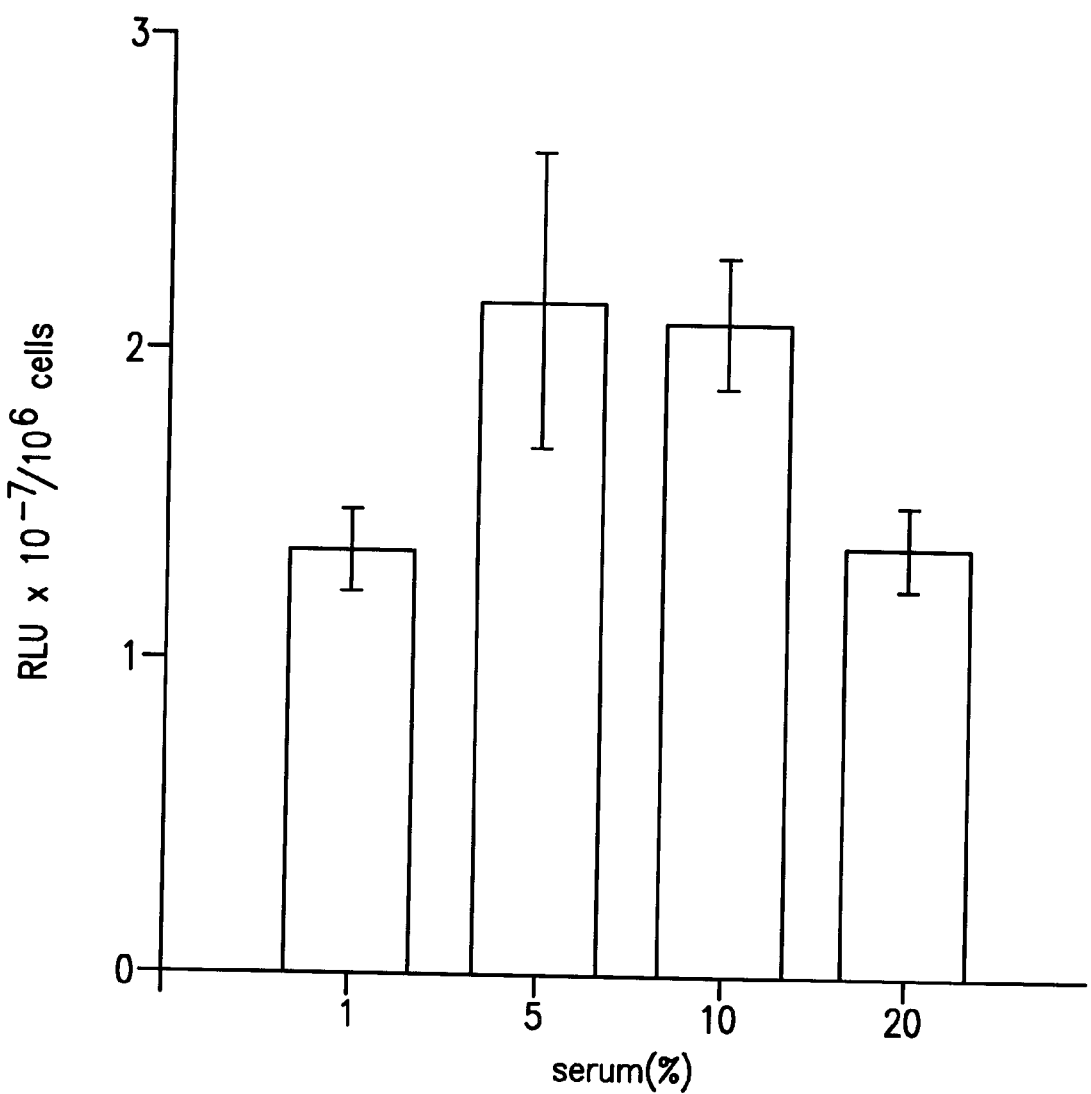
Figure 9:
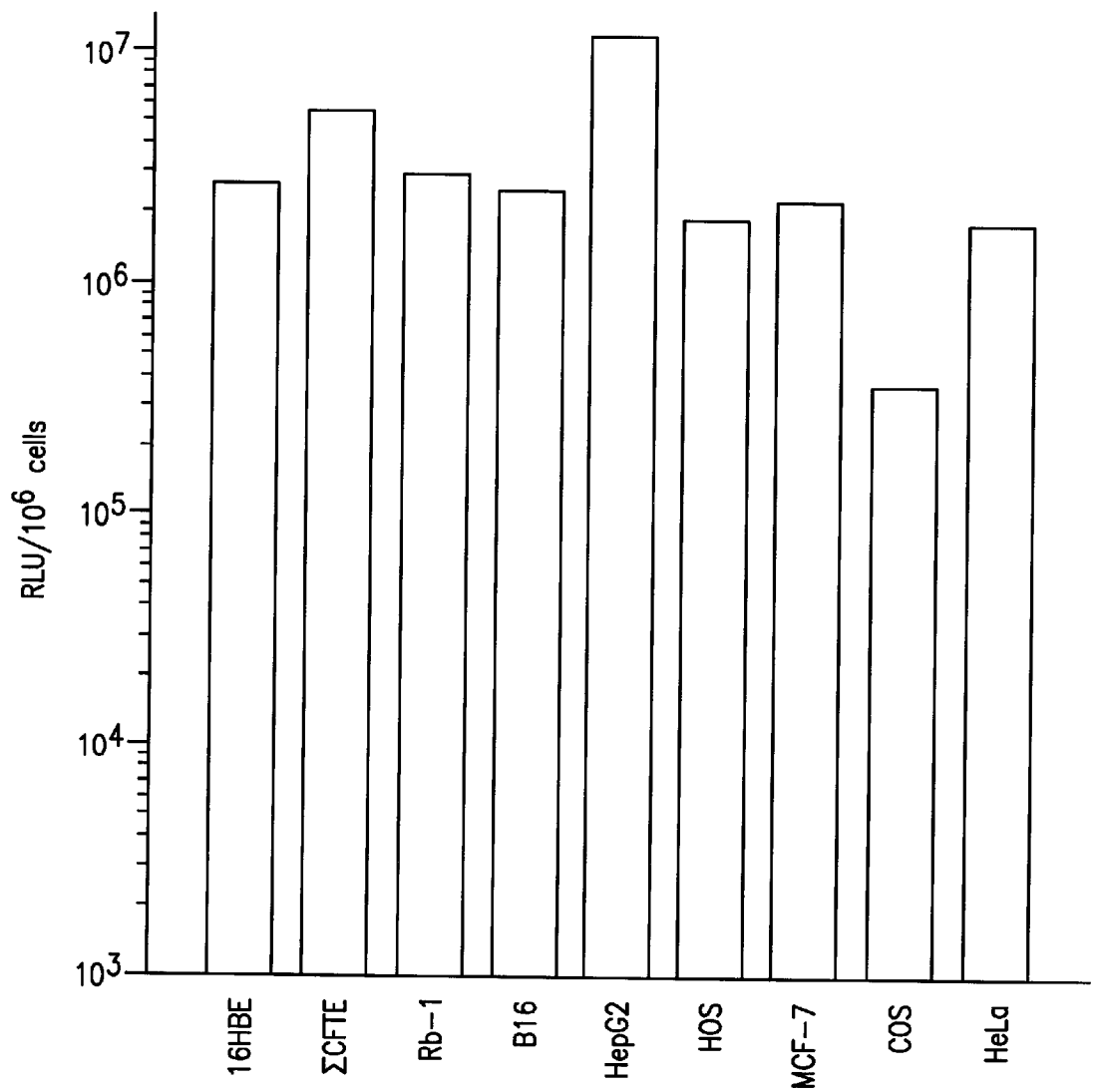

This shows a fragment of polylysine (DP 190) partly substituted by histidyl residues.

FIG. 2

This shows the NMR spectrum at 300 MHz in $D_2O$ of polylysine (DP 190) substituted by 70 histidyl residues:

1.28 to 1.88 ppm: 6 protons of carbons 3, 4 and 5 of substituted or unsubstituted lysines.

2.39 ppm: protons of the $CH_3$ group of p-toluenesulphonate 2.75 ppm: DMSO plot 2.99 ppm: 2 protons of carbon 6 of an unsubstituted lysyl residue 3.15 ppm: 2 protons of carbon 6 of a substituted lysyl residue 3.35 ppm: 2 protons of carbon 9 of a histidyl residue 4.36 ppm: 2 protons of carbons 2 and 8

4.78 ppm: peak of water 7.36 ppm: 2 protons (doublet, ortho-coupling constant= 7.97 Hz) of the protons of carbons 2 and 6 of the aromatic ring of p-toluenesulphonate 7.42 ppm: 1 proton of carbon 11 of a histidyl residue 7.71 ppm: 2 protons (doublet, ortho-coupling constant= 8.01 Hz) of the protons of carbons 3 and 5 of the aromatic ring of p-toluenesulphonate 8.7 ppm: 1 proton of carbon 12 of a histidyl residue.

FIG. 3

This relates to the preparation of polylysine (DP 190) partly substituted by 70 histidyl residues.

Poly-L-lysine in the hydrobromide form (average molecular weight 40,000; average degree of polymerization 190) (1 g in 200 ml $H_2O$) originating from Bachem Feinchemikalien (Budendorf, Switzerland) is first passed over an anion exchange column (Dowex 2×8, OH⁻ form; 35×2.5 cm) in order to remove the bromide, which is toxic to cells. The polylysine solution is neutralized with a 10% solution of p-toluenesulphonic acid in water and then lyophilized.

The polylysine is partly substituted with histidyl residues as follows: the polylysine in the form of the p-toluenesulphonate (50 mg; 0.96 μmole), dissolved in 3 ml DMSO (dimethylsulphoxide) in the presence of diisopropylethylamine (42 μl; 288 μmoles) is reacted for 24 hours at 20° C. with 32 mg (Boc)His(Boc)-OH (96 μmoles) in the presence of 43 mg benzotriazolyl-N-oxytrisdimethylaminophosphonium hexafluorophosphate (BOP) (97 μmoles). The histidyl residues are then deprotected in the presence of 20 ml of a mixture of water and trifluoroacetic acid (TFA) (50/50 V/V) for 24 hours at 20° C. The water and the TFA are removed by evaporation under reduced pressure. The polymer is precipitated by adding 10 volumes of isopropanol. After centrifugation (1,800 g×15 minutes), the residue is washed with isopropanol and collected after renewed centrifugation. The residue is taken up in distilled water and the solution is lyophilized. The number x of histidyl residues bonded per molecule of polylysine is determined by proton NMR as follows:

$$x = 6(h_{8.7}/h_{Lys})DP$$

where $h_{8.7}$ is the integral of the peak at 8.7 ppm corresponding to the proton of carbon 12 of a histidyl residue, $h_{Lys}$ is the integral of peaks between 1.28 and 1.88 ppm corresponding to 6 protons of carbons 3, 4 and 5 of lysine residues and DP is the degree of polymerization of the polylysine (DP=190). The number of histidyl residues bonded per molecule of polylysine is x, and x=70 in the preparation described above.

FIG. 4

The DNA/HispLK complexes are formed by mixing the plasmid pCMVLUC (10 μg in 0.7 ml DMEM) and the polylysine substituted by 70 histidyl residues (40 μg in 0.3 ml DMEM). After 30 minutes at 20° C., the solution containing the complexes is diluted once with DMEM and topped up with 5% fetal bovine serum. The DNA/pLK complexes are formed by mixing the plasmid pCMVLUC (10 μg in 0.7 ml DMEM) and the polylysine (5 μg in 0.3 ml in DMEM). After 30 minutes at 20° C., the solution containing the complexes is diluted once with DMEM and topped up with 5% fetal bovine serum and either with 100 μM chloroquine (+chloro) or 20 μM of a fusiogenic peptide (+E5CA) (GLFEAIAEFIEGGWEGLIEGCA; SEQ ID NO:7). The medium in which the HepG2 cells (3×10⁵ cells/4 cm²) have grown for 24 hours is removed and replaced by a solution (1 ml) containing a DNA/polymer complex (5 μg/ml DNA). After incubation for 4 hours at 37° C., the cell medium is removed again and the cells are incubated in culture medium in the presence of 10% fetal bovine serum. The expression of the gene of luciferase was determined 48 hours after the transfection by measuring the luminescence emitted (RLU: relative values of the light emitted expressed in arbitrary units) in the cell lysates for 4 seconds.

From left to right on the abscissa axis, the first rectangle corresponds to the DNA/histidylated polylysine complex, the second rectangle corresponds to the DNA/polylysine complex, the third rectangle corresponds to the DNA/polylysine complex to which chloroquine is added and the fourth rectangle corresponds to the DNA/polylysine complex to which the fusiogenic peptide E5CA is added.

In the box: change in the efficiency of the transfection as a function of the amount of plasmid.

FIG. 5

This relates to the transfer of genes into HepG2 cells using polylysine (DP 190) partly substituted by histidyl residues. It shows the influence of the number of histidyl residues bonded per molecule of polylysine on the efficiency of the transfection.

From left to right on the abscissa axis, the first rectangle corresponds to the DNA/unsubstituted polylysine complex, the second rectangle corresponds to the complex of DNA/polylysine substituted by 19 histidyl residues, the third rectangle corresponds to the complex of DNA/polylysine substituted by 30 histidyl residues, the fourth rectangle corresponds to the complex of DNA/polylysine substituted by 46 histidyl residues, the fifth rectangle corresponds to the complex of DNA/polylysine substituted by 63 histidyl residues, the sixth rectangle corresponds to the complex of DNA/polylysine substituted by 70 histidyl residues and the seventh rectangle corresponds to the complex of DNA/polylysine substituted by 84 histidyl residues.

The DNA/HispLK complexes are formed by mixing the plasmid pCMVLUC (10 μg in 0.7 ml DMEM) and the polylysine substituted by a varying number of histidyl residues (40 μg in 0.3 ml DMEM). After 30 minutes at 20° C., the solution containing the complexes is diluted once with DMEM and topped up with foetal bovine serum (final concentration 10%). The medium in which the HepG2 cells (3×10⁵ cells/4 cm²) have grown for 24 hours is removed and replaced by a solution (1 ml) containing a DNA/polymer complex (5 μg/ml DNA). After incubation for 4 hours at 37° C., the cell medium is removed again and the cells are incubated in culture medium in the presence of 10% foetal bovine serum. The expression of the gene of luciferase was determined 48 hours after the transfection by measuring the luminescence emitted (RLU: relative values of the light emitted expressed in arbitrary units) in the cell lysates for 4 seconds.

Under these conditions, 1 pg/ml luciferase produces 2,000 RLU.

FIG. 6

This relates to the transfer of genes into HOS cells using polylysine (DP 190) partly substituted by histidyl residues. It shows the influence of the DNA/polymer ratio (expressed on the abscissa in μg polymer per 100 μg DNA) in the pCMVLUC/His$_{84}$pLK complexes on the efficiency of the transfection.

The DNA/HispLK complexes are formed by mixing the plasmid pCMVLUC (10 μg in 0.7 ml DMEM) and various amounts of polylysine substituted by 84 histidyl residues in 0.3 ml DMEM. After 30 minutes at 20° C., the solution containing the complexes is diluted once with DMEM and topped up with 1% foetal bovine serum. The medium in which the HOS cells ($2\times10^5$ cells/4 cm$^2$) have grown for 24 hours is removed and replaced by a solution (1 ml) containing a DNA/polymer complex (5 μg/ml DNA). After incubation at 37° C. for 4 hours, the cell medium is removed again and the cells are incubated in culture medium in the presence of 10% foetal bovine serum. The expression of the gene of luciferase was determined 48 hours after the transfection by measuring the luminescence emitted (RLU: relative values of the light emitted expressed in arbitrary units) in the cell lysates for 4 seconds.

Under these conditions, 1 pg/ml luciferase produces 2,000 RLU.

FIG. 7

This relates to the transfer of genes into HepG2 cells using polylysine (DP 190) partly substituted by histidyl residues. It shows the influence of the incubation time (expressed in hours on the abscissa) of the pCMVLUC/His$_{70}$pLK complexes with the cells on the efficiency of the transfection. The DNA/HispLK complexes are formed by mixing the plasmid pCMVLUC (10 μg in 0.7 ml DMEM) and polylysine substituted by 70 histidyl residues (40 mg in 0.3 ml DMEM). After 30 minutes at 20° C., the solution containing the complexes is diluted once with DMEM and topped up with foetal bovine serum. The medium in which the HepG2 cells ($3\times10^5$ cells/4 cm$^2$) have grown for 24 hours is removed and replaced by a solution (1 ml) containing a DNA/polymer complex (5 μg/ml DNA). After incubation at 37° C. for various periods of time, the cell medium is removed again and the cells are incubated in culture medium in the presence of 10% foetal bovine serum. The expression of the gene of luciferase was determined 48 hours after the transfection by measuring the luminescence emitted (RLU: relative values of the light emitted expressed in arbitrary units) in the cell lysates for 4 seconds.

Under these conditions, 1 pg/ml luciferase produces 2,000 RLU.

FIG. 8

This relates to the transfer of genes into HepG2 cells using polylysine (DP 190) partly substituted by histidyl residues. It shows the influence of the amount of foetal bovine serum (expressed on the abscissa in % serum in the medium used) present during incubation of the pCMVLUC/His$_{70}$pLK complexes with the cells on the efficiency of the transfection. The DNA/HispLK complexes are formed by mixing the plasmid pCMVLUC (10 μg in 0.7 ml DMEM) and polylysine substituted by 70 histidyl residues (40 ug in 0.3 ml DMEM). After 30 minutes at 20° C., the solution containing the complexes is diluted once with DMEM and topped up with various amounts of foetal bovine serum. The medium in which the HepG2 cells ($3\times10^5$ cells/4 cm$^2$) have grown for 24 hours is removed and replaced by a solution (1 ml) containing a DNA/polymer complex (5 μg/ml DNA). After incubation at 37° C. for 4 hours, the cell medium is removed again and the cells are incubated in culture medium in the presence of 10% foetal bovine serum. The expression of the gene of luciferase was determined 48 hours after the transfection by measuring the luminescence emitted (RLU: relative values of the light emitted expressed in arbitrary units) in the cell lysates for 4 seconds.

Under these conditions, 1 pg/ml luciferase produces 2,000 RLU.

FIG. 9

This relates to the transfer of genes into various cell lines using polylysine (DP 190) substituted by 84 histidyl residues. The DNA/HispLK complexes are formed by mixing the plasmid pCMVLUC (10 μg in 0.7 ml DMEM) and polylysine substituted by 84 histidyl residues in 0.3 ml DMEM. After 30 minutes at 20° C., the solution containing the complexes is diluted once with DMEM and topped up to 10% with foetal bovine serum. The medium in which the cells ($2-3\times10^5$ cells/4 cm$^2$) have grown for 24 hours is removed and replaced by a solution containing a DNA/polymer complex (5 μg/ml DNA). After incubation at 37° C. for 4 hours, the cell medium is removed again and the cells are incubated in culture medium in the presence of 10% foetal bovine serum. The expression of the gene of luciferase was determined 48 hours after the transfection by measuring the luminescence emitted (RLU: relative values of the light emitted expressed in arbitrary units) in the cell lysates for 4 seconds. HepG2=cell line derived from a human hepatocarcinoma; HOS=cell line derived from a human osteosarcoma; MCF-7 cell line derived from a human adenocarcinoma; B16=cell line derived from a murine melanoma; COS=cell line derived from cells of the kidneys of the monkey transformed by SV40; Rb1=cell line derived from smooth muscle cells of the aorta of the rabbit; HeLa=human epitheloid cell line; 16 HBE=epithelial cell line of the normal human respiratory tract; ΣCFTE=epithelial cell line of the human respiratory tract deficient with respect to the gene responsible for cystic fibrosis (CFTR).

PREPARATION OF HISTIDYLATED POLYLYSINE SUBSTITUTED BY LACTOSE

Preparation of Polylysine Substituted by Activated Thiol Groupings

Polylysine in the hydrobromide form (average molecular weight 40,000; average degree of polymerization 190) (1 g in 200 ml H$_2$O) originating from Bachem Feinchemikalien (Budendorf, Switzerland) is first passed over an anion exchange column (Dowex 2×8, OH$^-$ form; 35×2.5 cm) in order to remove the bromide, which is toxic to cells. The polylysine solution is neutralized with a 10% solution of p-toluenesulphonic acid in water and then lyophilized.

The polylysine p-toluenesulphonate (50 mg; 0.91 μmole) is dissolved in 2 ml DMSO and reacted at 20° C. for 12 h with the N-hydroxysuccinimide ester of 4-carbonyl-α-methyl-α-(2-pyridinyldithio)toluene (SMPT, Pierce, USA) (5.3 mg; 13.6 μmoles). The polylysine substituted by carbonyl-α-methyl-α-(2-pyridinyldithio)toluene groups (=MPT-pLK) is precipitated by adding 10 volumes of isopropanol. After centrifugation (1,800 g×15 minutes), the residue is washed with isopropanol and recovered after renewed centrifugation. The residue is taken up in distilled water and the solution is lyophilized. The average number of MPT molecules bonded per molecule of polylysine is determined by the absorbance at 343 nm of pyridinethione ($\epsilon = 8,080$ M$^{-1}$×cm$^{-1}$) released by quantitative reduction of the disulphide bond with the aid of TCEP (tris-carboxyethylphosphine): the average number of MPT per molecule of polylysine is 10.

Preparation of Histidylated Polylysine Substituted by Activated Thiol Groupings

Polylysine in the form of the p-toluenesulphonate substituted by 10 residues of MPT (50 mg; 0.96 µmole), dissolved in 3 ml DMSO (dimethylsulphoxide) in the presence of diisopropylethylamine (42 µl; 288 µmoles), is reacted for 24 hours at 20° C. with 32 mg (Boc)His(Boc)-OH (80 µmoles) in the presence of 43 mg benzotriazolyl-N-oxytrisdimethylaminophosphonium hexafluorophosphate (BOP) (97 µmoles). The histidyl residues are then deprotected in the presence of 20 ml of a mixture of water and trifluoroacetic acid (TFA) (50/50 V/V) to the extent of 50% for 24 hours at 20° C. The water and the TFA are removed by evaporation under reduced pressure. The polymer is precipitated by adding 10 volumes of isopropanol. After centrifugation (1,800 g×15 minutes), the residue is washed with isopropanol and collected after renewed centrifugation. The residue is taken up in distilled water and the solution is lyophilized. The number of histidyl residues bonded per molecule of polylysine, determined by proton NMR, is 60.

Reduction of Dithiopyridyl

The oligoside is first converted into the glycopeptide by a method described in French Patent Application 9407738 (Monsigny M., Sdiqui N., Roche A. C. and Mayer R., 1994, Nouveaux dérivés d'oligosides, leur procédé de préparation et leurs applications [New derivatives of oligosides, a process for their preparation and their uses]).

The glycopeptide is bonded to the partly histidylated polylysine via a disulphide bridge.

The Galβ4Glcβ-pyroglutamyl-NH—(CH$_2$)$_2$—S—S-pyridine (3 µmoles) is treated with 3.5 µmoles TCEP (tris-carboxyethylphosphine) in a sodium phosphate buffer, 0.1 M, at pH 7 (1 ml) for 1 h at 20° C. This solution is added to the partly histidylated polylysine substituted by 10 residues of MPT (10 mg; 0.2 µmole), dissolved in the sodium phosphate buffer, 0.1 M at pH 7 (1 ml). After 1 h at 20° C., the polymer is precipitated by addition of 10 volumes of isopropanol. The precipitate is collected after centrifugation (1,800 g, 15 min) and washed in isopropanol and then dissolved in water and lyophilized.

The yield of the coupling reaction under the conditions used is equal to or greater than 90%.

Preparation of Histidylated Polylysine Substituted by a Complex Oligoside: Lewis$^b$ Example of Lewis$^b$=Fucα4(Fucα2Galβ3)GlcNAcβ3Galβ4Glc Complex oligosides having a glucose (Glc) or N-acetylglucosamine (GlcNAc) residue in a reducing position are first converted into glycopeptides by a method described in French Patent Application 9407738 (Monsigny M., Sdiqui N., Roche A. C. and Mayer R., (1994) Nouveaux dérivés d'oligosides, leur procédé de préparation et leurs applications [New derivatives of oligosides, a process for their preparation and their uses]).

The complex oligosides are bonded to the partly histidylated polylysine by bonding of the glycopeptide to the histidylated polylysine via a disulphide bridge.

The oligoside Fucα4(Fucα2Galβ3)GlcNAcβ3Galβ4Glc is converted into the glycopeptide derivative Fucα4(Fucα2Galβ3)GlcNAcβ3Galβ4Glcβ-pyroglutamyl-R. The carboxyl group of pyroglutamyl is substituted by a dithiopyridine function to give the glycopeptide: Fucα4(Fucα2Galβ3)GlcNAcβ3Galβ4Glcβ-pyroglutamyl-NH—(CH$_2$)$_2$—S—S-pyridine (French Patent Application 9407738: Monsigny M., Sdiqui N., Roche A. C. and Mayer R., 1994, Nouveaux dérivés d'oligosides, leur procédé de préparation et leurs applications [New derivatives of oligosides, a process for their preparation and their uses] and Quétard et al., Simple synthesis of novel glycosynthons for glycoconjugate preparation: oligosylpyroglutamyl derivatives, in preparation).

Glycopeptide Reduction

The glycopeptide (2 µmoles) is treated with 2.2 µmoles TCEP (tris-carboxyethylphosphine) in a sodium phosphate buffer, 0.1 M at pH 7 (1 ml) for 1 h at 20° C. This solution is added to the partly histidylated polylysine substituted by 10 residues of MPT (10 mg; 0.2 mole), dissolved in the sodium phosphate buffer, 0.1 M at pH 7 (1 ml). After 1 h at 20° C., the polymer is precipitated by addition of 10 volumes of isopropanol. The precipitate is collected after centrifugation (1,800 g, 15 min) and washed in isopropanol and then dissolved in water and lyophilized.

The yield of the coupling reaction under the conditions used is equal to or greater than 90%.

Preparation of Histidylated Polylysine Substituted by the Peptide ANP

Preparation of Polylysine Substituted by Activated Thiol Groupings

Polylysine in the hydrobromide form (average molecular weight 40,000; average degree of polymerization 190) (1 g in 200 ml H$_2$O) originating from Bachem Feinchemikalien (Budendorf, Switzerland) is first passed over an anion exchange column (Dowex 2×8, OH$^-$ form; 35×2.5 cm) in order to remove the bromide, which is toxic to cells. The polylysine solution is neutralized with a 10% solution of p-toluenesulphonic acid in water and then lyophilized.

The polylysine p-toluenesulphonate (50 mg; 0.91 µmole) is dissolved in 2 ml DMSO and reacted at 20° C. for 12 h with the N-hydroxysuccinimide ester of 4-carbonyl-α-methyl-α-(2-pyridinyldithio)toluene (SMPT, Pierce, USA) (5.3 mg; 13.6 µmoles). The polymer (MPT-pLK) is precipitated by adding 10 volumes of isopropanol. After centrifugation (1,800 g×15 minutes), the residue is washed with isopropanol and recovered after renewed centrifugation. The residue is taken up in distilled water and the solution is lyophilized. The average number of MPT molecules bonded per molecule of polylysine is determined by the absorbance at 343 nm of pyridinethione ($\epsilon$=8,080 M$^{-1}$×cm$^{-1}$) released by quantitative reduction of the disulphide bond with the aid of TCEP: the average number of MPT is 10.

Preparation of Histidylated Polylysine Substituted by Activated Thiol Groupings

Polylysine in the form of the p-toluenesulphonate substituted by 10 residues of MPT (50 mg; 0.96 µmole), dissolved in 3 ml DMSO (dimethylsulphoxide) in the presence of diisopropylethylamine (42 µl; 288 µmoles), is reacted for 24 hours at 20° C. with 32 mg (Boc)His(Boc)-OH (80 µmoles) in the presence of 43 mg benzotriazolyl-N-oxytrisdimethylaminophosphonium hexafluorophosphate (BOP) (97 µmoles). The histidyl residues are then deprotected in the presence of 20 ml of a 50% solution of trifluoroacetic acid (TFA) for 48 hours at 20° C. The water and the TFA are removed by evaporation under reduced pressure. The polymer is precipitated by adding 10 volumes of isopropanol. After centrifugation (1,800 g×15 minutes), the residue is washed with isopropanol and collected after renewed centrifugation. The residue is taken up in distilled water and the solution is lyophilized. The number x of histidyl residues bonded per molecule of polylysine, determined by proton NMR, is 60.

Reduction of the Peptide ANP

The peptide ANP (CYSLRRSSAFGGRIDRIGAQSA) with its cysteine in the N-terminal position protected in the form of thiopyridinyl (7.5 mg; 2 µmoles) is reacted at 20° C. for 15 minutes with TCEP (0.7 mg; 2 µmoles) in 1 ml of buffer, 0.1 M NaCl, 0.1 M tris/HCl pH 7.6.

Preparation of Histidylated Polylysine Substituted with the Peptide ANP

The partly histidylated polylysine substituted by 10 molecules of MPT (MPT$_{10-}$,His$_{70}$pLK (10 mg; 0.2 µmole) in 1 ml of buffer, 0.1 M NaCl, 0.1 M tris/HCl pH 7.6, is reacted at 20° C. for 24 hours with 7.5 mg (2 µmoles) of peptide ANP, the cysteine of which has been reduced. The polymer (ANP-S-,His$_{70}$-pLK) is precipitated by adding 10 volumes of isopropanol. After centrifugation (1,800 g×15 minutes), the residue is washed with isopropanol and collected after renewed centrifugation. The residue is taken up in distilled water and the solution is lyophilized. The average number of molecules of peptide ANP bonded per molecule of polymer is determined by analysis of the amino acids of the polymer by high pressure chromatography (HPLC) with a C$_{18}$ reversed phase column (Supelcosil LC-18-DB, Supelco, Bellefonte, Pa., USA), after hydrolysis of the polymer in HCl 5.6 N at 105° C. for 72 hours and conversion of the amino acids liberated into phenylthiohydantoin derivatives (PTH-aa). The average number of ANP per molecule of polymer is 8.

Preparation of Histidylated Polylysine Substituted by Biotin

Polylysine substituted by 60 histidyl residues (15 mg; 0.28 µmole), dissolved in 1 ml DMSO in the presence of DIEA (4 µl; 28 µmoles) is reacted for 7 h at 20° C. with the N-hydroxysuccinimide ester of 6-(biotinamido)hexanoate (NHS-LC-biotin, Pierce, USA). The polymer is precipitated by addition of 10 volumes of isopropanol. The precipitate is collected after centrifugation (1,800 g, 15 min) and washed in isopropanol and then dissolved in water and lyophilized.

What is claimed is:

1. A complex comprised of at least one negatively charged nucleic acid and at least one positively charged polymeric conjugate with the bond therebetween being electrostatic in nature, the polymeric conjugate containing a polylysine formed from monomers having free $NH_3^+$ groups, at least 10% of free $NH_3^+$ groups of the said polylysine are substituted by residues which are protonated in a weakly acid medium causing destabilization of cell membranes, and optionally at least one free $NH_3^+$ group of the said polylysine is substituted by a molecule with a recognition signal recognized by a cell membrane receptor, with the proviso that all the free $NH_3^+$ groups of the said polysinc make up at least 30% of the number of monomers of the skeleton of the polymeric conjugate, wherein said residues causing destabilization of cell membrane in a weakly acid medium belong to the family of quinolines of the formula:

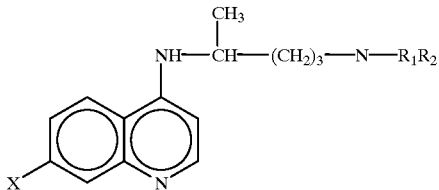

in which $R_1$ is hydrogen, $R_2$ is $—(CH_2)_n—CO_2—H$, X is hydrogen or chlorine and n is an integer from 1 to 10, wherein said recognition signal is selected from the group consisting of:

a) simple osides selected from the group consisting of α or β conformers of 2-deoxy, 2-amino or 2deoxy, 2-acetamido neutral monosaccharides; α or β conformers of glycuronic acid derivatives of neutral monosaccharides; α or β conformers of L-iduronic acid, of keto-deoxy-octonic acid, of N-acetyl neuraminic acid, or of N-glycoloyl-neuraminic acid; and α or β conformers of neutral 6-deoxy monosaccharides;

b) a disaccharide selected from the group consisting of lactose and mannopyranosyl α-6-mannopyranose, c) complex osides selected from the group consisting of Lewis$^a$, Lewis$^b$, Lewis$^x$, oligomannosides and oligolactiosamines and d) peptides.

2. The complex of claim 1 wherein said quinolines are selected from the group consisting of 7-chloro-4-(amino-1-methyl-butylamino)-quinoline, N$^4$-(7-chloro-4-quinolinyl)-1,4-pentanediamine, 8-(4-amino-1-methylbutylamino)-6methoxyquinoline (primaquine), N$^4$-(6-methoxy-8-qunolinyl)-1,4-pentanediamine, and pyridines selected from the group consisting of nicotinic acid and quinolenic acid and pterines.

3. The complex of claim 1 wherein the free NH$_3^+$ groups of the polylysine are substituted with a non-charged gluconyl residue causing a reduction in the positive charge of the polymeric conjugate which facilitates salting out of the nucleic acids upon dissociation of the complex.

4. The complex of claim 1 wherein said recognition-signal is a peptide chosen from the group consisting of (a) anti-inflammatory peptides recognized by receptors of the vascular wall, (b) ligand peptides of integrins, (c) chemiotactic factors and (d) peptide hormones.

5. The complex of claim 1 wherein:

the monosaccharide are selected from the group consisting of galactose, mannose, fucose, glucose, ribose, xylose and rhamnose and the complex osides are selected from the group consisting of (a) Asialo-oligoside of the type of triantennar lactosamine of

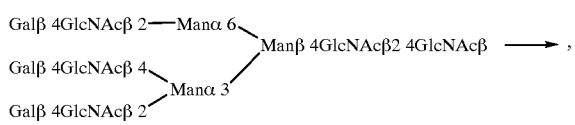

(b) Asialo-oligoside of the type of tetraanetennar lactosamin of the formula

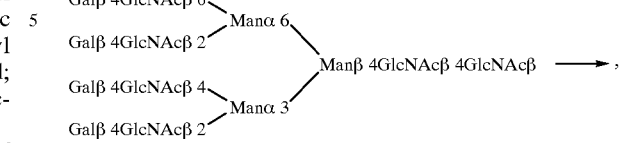

(c) Lewis x of the formula

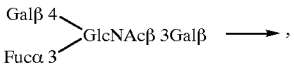

(d) Lewis x sialyl of the formula

(e) Sulphated Lewis x derivative (HNK1) of the formula

(f) Oligomannoside of the formula

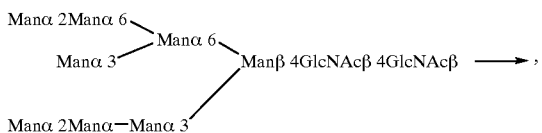

(g) Phosphorylated oligomannoside

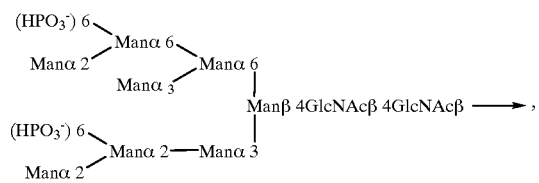

(h) Oligosaccharide of the type of sulphated lactosamine of the formula

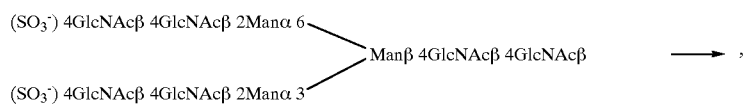

i. Lactose, j. Fucα2Gakβ3 (fucα4) GlcNAcβ1Galβ3Glc, k. Fucα4 (Gaβ3) GlcNAcβ3Galβ and l. Manα6-man.

6. The complex of claim 5 wherein the peptides are selected from the group consisting of vasodilator intestinal polypeptide (VIP)

HSDAVFTDNYTRLRKQMAVKKYLNSILN-NH$_2$ (SEQ ID No: 2)
antrial natriuretic polypeptide (ANP)
SLRRSSCFGGRMDRIGAQSGLGCNSFRY (SEQ ID No: 3)
lipocortin
HDMNKVLDL (SEQ ID No: 4)
bradykinin
RPPGFSPER (SEQ ID No: 5);
  peptides of intergrins, peptide hormones and chemotactics factors.
7. The complex of claim 1 wherein the polymeric conjugate has the formula:

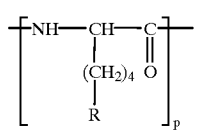

wherein
  p is an integer from 15 to 900,
  10 to 45% of the radical R being a residue with an imidazole nucleus,
  10 to 90% of R being free NH$_3^+$ groups,
  and optionally 0 to 45% of R being —NH—CO—(CHOH)$_m$—R$_1$, m is an integer from 2 to 15, and R$_1$ is hydrogen or alkyl of 1 to 15 carbon atoms.
8. The complex of claim 7 wherein R is a residue with an imidazole nucleus of the formula:

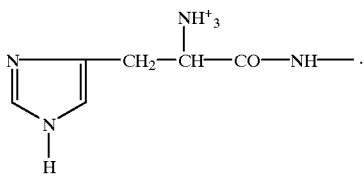

9. The complex of claim 7 wherein the polymeric conjugate has the following formula:

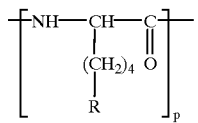

wherein
  p is an integer from 15 to 900,
  10% to 45% of R is a residue having an imidazole nucleus and optionally a free NH$_3^+$, R has the formula:

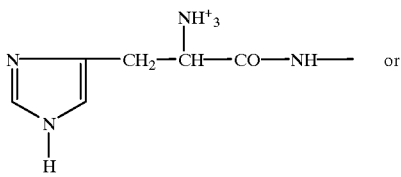

30% to 90% of the number of R, having free NH$_3^+$, and 0 to 45% of R are substituted by a molecule which constitutes a recognition signal by a cell membrane receptor, with the proviso that all the free NH$_3^+$ functions make up at least 30% of the number of monomer units of the polymeric skeleton of the above mentioned polymeric conjugate.

10. A complex according to claim 1 wherein the nucleic acid is selected from the group consisting of:
  a) marker genes and
  b) genes encoding a therapeutic protein.

11. Positively charged polymeric conjugate containing a polylysine formed from monomers having free NH$_3^+$ groups:
  at least 10% of the free NH$_3^+$ groups of the said polylysine are substituted by residues which are protonated in a weakly acid medium causing destabilization of cell membranes,
  and optionally some of the free NH$_3^+$ groups of the said polylysine can be substituted by a molecule with a recognition signal recognized by a cell membrane receptor,
  with the proviso that all the free NH$_3^+$ groups of the said polylysine make up at least 30% of the number of monomers of the skeleton of the polymeric conjugate,
  wherein said residues causing destabilization of cell membranes in a weakly acid medium belong:
  to the family of quinolines of the formula

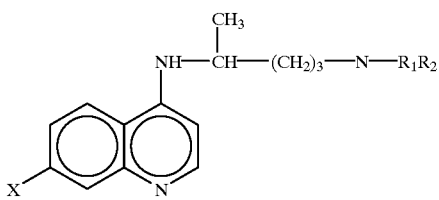

in which R$_1$ is hydrogen, R$_2$ is (CH$_2$)$_n$—CO$_2$—H, X is hydrogen or chlorine and n is an integer from 1 to 10, wherein said recognition signal is selected from the group consisting of:
  simple osides selected from the group consisting of α or β conformers of 2-deoxy, of 2-amino or of 2-deoxy, 2-acetamido neutral monosaccharides; α or β conformers of glycuronic acid derivatives of neutral monosaccharides; α or β conformers of L-iduronic acid, of keto-deoxy-octonic acid, of M-acetyl-neuraminic acid, or of N-glycoloyl-neuraminic acid; and α or β conformers of neutral 6-deoxy monosaccharides;
  a disaccharide selected from the group consisting of lactose and mannopyranosylα-6-mannopyranose,
  and complex osides selected from the group consisting of Lewis$^a$, Lewis$^b$, Lewis$^z$, oligomannosides and oligolactosamines, and peptides.

12. The positively charged polymeric conjugate according to claim 11 wherein the free NH$_3^+$ groups of the polylysine are substituted with a non-charged residue causing a reduction in the positive charge of the polymeric conjugate which facilitates salting out of the nucleic acids upon dissociation of the complex, said non-charged residue being a gluconyl.

13. The composition comprising the complex of claim 1 and an inert pharmaceutical carrier.

14. A method of transfecting cultured cells comprising incubating said cells in the presence of the composition of claim 13 under conditions wherein said composition enters said cells, and the nucleic acid comprised in the complex of said composition is released to transfect cultured cells.

15. The method of claim 14 wherein the cells are selected from the group consisting of
  cells of hematopoietic strains;
  dendritic cells;
  liver cells;
  skeletal muscle cells;
  skin cells;
  fibroblasts,
  keratinocytes,
  dendritic cells,
  melanocytes;
  cells of the vascular walls;
    endothelial;
    smooth muscle;
  epithelial cells of the respiratory tract;
  cells of the central nervous system;
  cancerous cells; and
  cells of the immune system.

* * * * *

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 1

Gly Ala Leu Ala
  1

<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence: VASODILATER
      INTESTINAL POLYPEPTIDE

<400> SEQUENCE: 2

His Ser Asp Ala Val Phe Thr Asp Asn Tyr Thr Arg Leu Arg Lys Gln
  1               5                  10                  15

Met Ala Val Lys Lys Tyr Leu Asn Ser Ile Leu Asn
             20                  25

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: ATRIAL
      NATRIURETIC POLYPEPTIDE

<400> SEQUENCE: 3

Ser Leu Arg Arg Ser Ser Cys Phe Gly Gly Arg Met Asp Arg Ile Gly
  1               5                  10                  15

Ala Gln Ser Gly Leu Gly Cys Asn Ser Phe Arg Tyr
             20                  25

<210> SEQ ID NO 4
```

```
<211> LENGTH: 9
<212> TYPE: PRT
<213> ORGANISM: Artificial Sequence
<220> FEATURE:
<223> OTHER INFORMATION: Description of Artificial Sequence: LIPOCORTIN
      SYNTHETIC PEPTIDE

<400> SEQUENCE: 4

His Asp Met Asn Lys Val Leu Asp Leu
  1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: BRADYKININ
      SYNTHETIC PEPTIDE

<400> SEQUENCE: 5

Arg Pro Pro Gly Phe Ser Pro Phe Arg
  1               5

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: SYNTHETIC
      PEPTIDE HORMONE

<400> SEQUENCE: 6

Ser Tyr Ser Met Glu His Phe Arg Trp Gly Lys Pro Val
  1               5                  10

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence:  FUSIOGENIC
      PEPTIDE

<400> SEQUENCE: 7

Gly Leu Phe Glu Ala Ile Ala Glu Phe Ile Glu Gly Gly Trp Glu Gly
  1               5                  10                  15

Leu Ile Glu Gly Cys Ala
              20
```